(12) United States Patent
Finke et al.

(10) Patent No.: US 7,196,113 B2
(45) Date of Patent: Mar. 27, 2007

(54) LACTAM TACHYKININ RECEPTOR ANTAGONISTS

(75) Inventors: Paul E. Finke, Miltown, NJ (US); Laura C. Meurer, Scotch Plains, NJ (US); Sander G. Mills, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 72 days.

(21) Appl. No.: 11/135,240

(22) Filed: May 23, 2005

(65) Prior Publication Data
US 2005/0282886 A1     Dec. 22, 2005

Related U.S. Application Data

(60) Provisional application No. 60/581,786, filed on Jun. 22, 2004.

(51) Int. Cl.
*A61K 31/4015* (2006.01)
*C07D 207/273* (2006.01)
(52) U.S. Cl. ...................... 514/424; 548/550
(58) Field of Classification Search ............... 514/424; 548/550
See application file for complete search history.

(56) References Cited

U.S. PATENT DOCUMENTS

| 5,387,595 A | 2/1995 | Mills et al. |
| 5,750,549 A | 5/1998 | Caldwell et al. |
| 5,877,191 A | 3/1999 | Caldwell et al. |
| 2002/0042431 A1 | 4/2002 | Finke et al. |

FOREIGN PATENT DOCUMENTS

WO    WO 97/14671    4/1997

*Primary Examiner*—Joseph K. McKane
*Assistant Examiner*—Jason M. Nolan
(74) *Attorney, Agent, or Firm*—Raynard Yuro; David L. Rose; J. Eric Thies

(57) ABSTRACT

The present invention is directed to certain lactam compounds which are useful as neurokinin-1 (NK-1) receptor antagonists, and inhibitors of tachykinin and in particular substance P. The invention is also concerned with pharmaceutical formulations comprising these compounds as active ingredients and the use of the compounds and their formulations in the treatment of certain disorders, including emesis, urinary incontinence, depression, and anxiety.

18 Claims, No Drawings

LACTAM TACHYKININ RECEPTOR ANTAGONISTS

CROSS REFERENCE TO RELATED APPLICATIONS

This application claims the benefit of priority under 35 U.S.C. 119 from provisional application U.S. 60/581,786, filed Jun. 22, 2004.

BACKGROUND OF THE INVENTION

Substance P is a naturally occurring undecapeptide belonging to the tachykinin family of peptides, the latter being so-named because of their prompt contractile action on extravascular smooth muscle tissue. The tachykinins are distinguished by a conserved carboxyl-terminal sequence. In addition to substance P, the known mammalian tachykinins include neurokinin A and neurokinin B. The current nomenclature designates the receptors for substance P, neurokinin A, and neurokinin B as neurokinin-1 (NK-1), neurokinin-2 (NK-2), and neurokinin-3 (NK-3), respectively. Tachykinin, and in particular substance P, antagonists are useful in the treatment of of clinical conditions which are characterized by the presence of an excess of tachykinin, in particular substance P, activity, including disorders of the central nervous system, nociception and pain, gastrointestinal disorders, disorders of bladder function and respiratory diseases. Attempts have been made to provide antagonists for the receptors of substance P and other tachykinin peptides in order to more effectively treat the various disorders and diseases mentioned above. For example, U.S. Pat. Nos. 5,387,595, 5,750,549, 5,877,191, 6,479,518 and Bioorg. & Med. Chem. Lett., 1345 (1995) disclose certain compounds as tachykinin receptor antagonists.

SUMMARY OF THE INVENTION

The present invention is directed to certain aminolactam compounds which are useful as neurokinin-1 (NK-1) receptor antagonists, and inhibitors of tachykinin and in particular substance P. The invention is also concerned with pharmaceutical formulations comprising these compounds as active ingredients and the use of the compounds and their formulations in the treatment of certain disorders, including emesis, urinary incontinence, depression, and anxiety.

DETAILED DESCRIPTION OF THE INVENTION

The present invention is directed to compounds of the formula I:

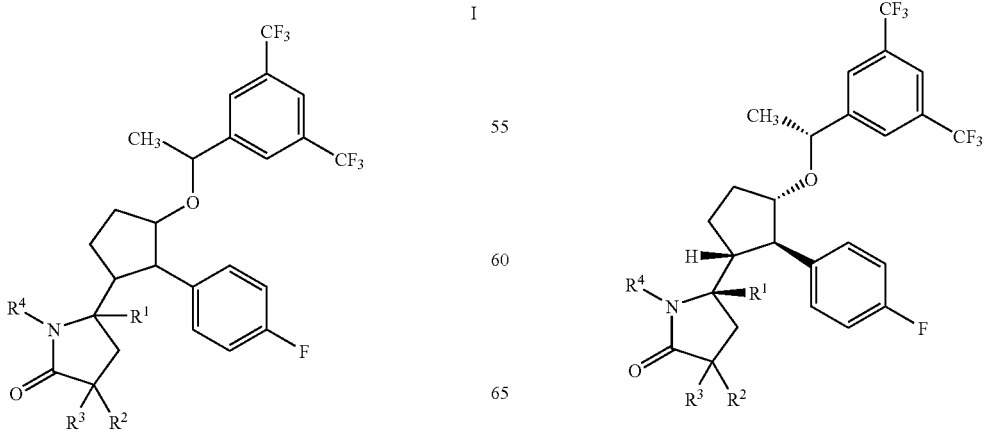

wherein:
R¹ is selected from the group consisting of:
  (1) hydrogen, and
  (2) $C_{1-6}$alkyl;
R² is selected from the group consisting of:
  (1) hydrogen,
  (2) —OH,
  (3) —NH$_2$,
  (4) —NH($C_{1-6}$alkyl), and
  (5) —N($C_{1-6}$alkyl)($C_{1-6}$alkyl);
R³ is selected from the group consisting of:
  (1) hydrogen, and
  (2) $C_{1-6}$alkyl;
R⁴ is selected from the group consisting of:
  (1) hydrogen, and
  (2) $C_{1-6}$alkyl;
and pharmaceutically acceptable salts thereof and individual enantiomers and diastereomers thereof.

An embodiment of the present invention includes compounds of the formula Ia:

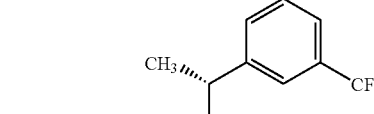

wherein R¹, R², R³ and R⁴ are defined herein;
and pharmaceutically acceptable salts thereof and individual enantiomers and diastereomers thereof.

An embodiment of the present invention includes compounds of the formula Ib:

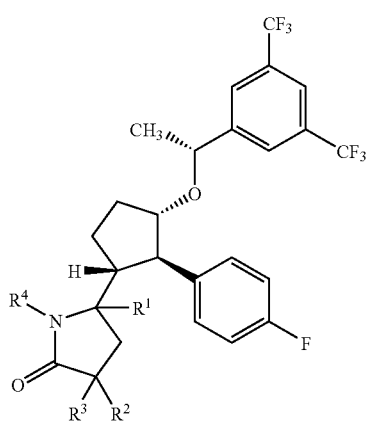

wherein $R^1$, $R^2$, $R^3$ and $R^4$ are defined herein;
and pharmaceutically acceptable salts thereof and individual enantiomers and diastereomers thereof.

An embodiment of the present invention includes compounds of the formula Ic:

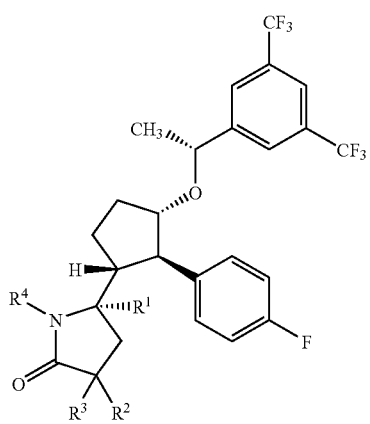

Ib wherein $R^1$, $R^2$, $R^3$ and $R^4$ are defined herein;
and pharmaceutically acceptable salts thereof and individual enantiomers and diastereomers thereof.

An embodiment of the present invention includes compounds wherein $R^1$ is selected from the group consisting of:
(1) hydrogen, and
(2) methyl.

Within this embodiment the present invention includes compounds wherein $R^1$ is hydrogen.

An embodiment of the present invention includes compounds wherein $R^2$ is selected from the group consisting of:
(1) hydrogen,
(2) —OH,
(3) —$NH_2$,
(4) —$NH(CH_3)$, and
(5) —$N(CH_3)(CH_3)$.

Within this embodiment the present invention includes compounds wherein $R^2$ is hydrogen. Also within this embodiment the present invention includes compounds wherein $R^2$ is —OH. Also within this embodiment the present invention includes compounds wherein $R^2$ is —$NH_2$.

An embodiment of the present invention includes compounds wherein $R^3$ is selected from the group consisting of:
(1) hydrogen, and
(2) methyl.

Within this embodiment the present invention includes compounds wherein $R^3$ is hydrogen. Also within this embodiment the present invention includes compounds wherein $R^3$ is methyl.

An embodiment of the present invention includes compounds wherein $R^4$ is selected from the group consisting of:
(1) hydrogen, and
(2) methyl.

Within this embodiment the present invention includes compounds wherein $R^4$ is hydrogen.

Specific embodiments of the present invention include a compound which is selected from the group consisting of the subject compounds of the Examples herein and pharmaceutically acceptable salts thereof and individual enantiomers and diastereomers thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without preferred stereochemistry. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halo or halogen as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl and hexyl. A group which is designated as being independently substituted with substituents may be independently substituted with multiple numbers of such substituents.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are benzenesulfonic, citric, hydrobromic, hydrochloric, maleic, fumaric, succinic and tartaric acids. It will be understood that, as used herein, references to the compounds of the present invention are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The compounds of the present invention are useful in the prevention and treatment of a wide variety of clinical conditions which are characterized by the presence of an excess of tachykinin, in particular substance P, activity. Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances), caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis. Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia, frequent urination and urinary incontinence, including the prevention or treatment of overactive bladder with symptoms of urge urinary incontinence, urgency, and frequency; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine. The compounds of the present invention are also of value in the treatment of a combination of the above conditions, in particular in the treatment of combined post-operative pain and post-operative nausea and vomiting.

The compounds of the present invention are particularly useful in the prevention or treatment of emesis, including acute, delayed or anticipatory emesis, such as emesis induced by chemotherapy, radiation, toxins, pregnancy, vestibular disorders, motion, surgery, migraine, and variations in intercranial pressure. For example, the compounds of the present invention are of use optionally in combination with other antiemetic agents for the prevention of acute and delayed nausea and vomiting associated with initial and repeat courses of moderate or highly emetogenic cancer chemotherapy, including high-dose cisplatin. Most especially, the compounds of the present invention are of use in the treatment of emesis induced by antineoplastic (cytotoxic) agents, including those routinely used in cancer chemotherapy, and emesis induced by other pharmacological agents, for example, rolipram. Examples of such chemotherapeutic agents include alkylating agents, for example, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics. Particular examples of chemotherapeutic agents are described, for instance, by D. J. Stewart in *Nausea and Vomiting: Recent Research and Clinical Advances,* Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine, streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172]. A further aspect of the present invention comprises the use of a compound of the present invention for achieving a chronobiologic (circadian rhythm phase-shifting) effect and alleviating circadian rhythm disorders in a mammal. The present invention is further directed to the use of a compound of the present invention for blocking the phase-shifting effects of light in a mammal.

The present invention is further directed to the use of a compound of the present invention or a pharmaceutically acceptable salt thereof, for enhancing or improving sleep quality as well as preventing and treating sleep disorders and sleep disturbances in a mammal. In particular, the present invention provides a method for enhancing or improving sleep quality by increasing sleep efficiency and augmenting sleep maintenance. In addition, the present invention provides a method for preventing and treating sleep disorders and sleep disturbances in a mammal which comprising the administration of a compound of the present invention or a pharmaceutically acceptable salt thereof. The present invention is useful for the treatment of sleep disorders, including Disorders of Initiating and Maintaining Sleep (insomnias) ("DIMS") which can arise from psychophysiological causes, as a consequence of psychiatric disorders (particularly related to anxiety), from drugs and alcohol use and abuse (particularly during withdrawal stages), childhood onset DIMS, nocturnal myoclonus, fibromyalgia, muscle pain, sleep apnea and restless legs and non specific REM disturbances as seen in ageing.

The particularly preferred embodiments of the instant invention are the treatment of emesis, urinary incontinence, depression or anxiety by administration of the compounds of the present invention to a subject (human or companion animal) in need of such treatment.

The present invention is directed to a method for the manufacture of a medicament for antagonizing the effect of substance P at its receptor site or for the blockade of neurokinin-1 receptors in a mammal comprising combining a compound of the present invention with a pharmaceutical carrier or diluent. The present invention is further directed to a method for the manufacture of a medicament for the treatment of a physiological disorder associated with an excess of tachykinins in a mammal comprising combining a compound of the present invention with a pharmaceutical carrier or diluent.

The present invention also provides a method for the treatment or prevention of physiological disorders associated with an excess of tachykinins, especially substance P, which method comprises administration to a patient in need thereof of a tachykinin reducing amount of a compound of the present invention or a composition comprising a compound of the present invention. As used herein, the term "treatment" or "to treat" refers to the administration of the compounds of the present invention to reduce, ameliorate, or eliminate either the symptoms or underlying cause of the noted disease conditions, in a subject (human or animal) that suffers from that condition or displays clinical indicators thereof. The term "prevention" or "to prevent" refers to the administration of the compounds of the present invention to reduce, ameliorate, or eliminate the risk or likelihood of occurrence of the noted disease conditions, in a subject (human or animal) susceptible or predisposed to that condition.

The compounds of this invention are useful for antagonizing tachykinins, in particular substance P in the treatment of gastrointestinal disorders, central nervous system disorders, inflammatory diseases, pain or migraine and asthma in a mammal in need of such treatment. This activity can be demonstrated by the following assays.

Receptor Expression in COS: To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 ug of the plasmid DNA into 10 million COS cells was achieved by electroporation in 800 ul of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM HEPES pH 7.4) at 260 V and 950 uF using the IBI GENEZAPPER (IBI, New Haven, Conn.). The cells were incubated in 10% fetal calf serum, 2 mM glutamine, 100 U/ml penicillin-streptomycin, and 90% DMEM media (GIBCO, Grand Island, N.Y.) in 5% $CO_2$ at 37° C. for three days before the assay.

Stable Expression in CHO: To establish a stable cell line expressing the cloned human NK1R, the cDNA was subcloned into the vector pRcCMV (INVITROGEN). Transfection of 20 ug of the plasmid DNA into CHO cells was achieved by electroporation in 800 ul of transfection buffer suplemented with 0.625 mg/ml Herring sperm DNA at 300 V and 950 uF using the IBI GENEZAPPER (IBI). The transfected cells were incubated in CHO media [10% fetal calf serum, 100 U/ml pennicilin-streptomycin, 2 mM glutamine, 1/500 hypoxanthine-thymidine (ATCC), 90% IMDM media (JRH BIOSCIENCES, Lenexa, Kans.), 0.7 mg/ml G418 (GIBCO)] in 5% $CO_2$ at 37° C. until colonies were visible. Each colony was separated and propagated. The cell clone with the highest number of human NK1R was selected for subsequent applications such as drug screening.

Assay Protocol using COS or CHO: The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 ul of the cell suspension would give rise to about 10,000 cpm of specific $^{125}$I-SP binding (approximately 50,000 to 200,000 cells). In the binding assay, 200 ul of cells were added to a tube containing 20 ul of 1.5 to 2.5 nM of $^{125}$I-SP and 20 ul of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter. The activation of phospholipase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 0.025 uCi/ml of $^3$H-myoinositol by overnight incubation. The extracellular radioactivity is removed by washing with phosphate buffered saline. LiCl is added to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1 N HCl is added. Each well is sonicated at 4° C. and extracted with $CHCl_3$/methanol (1:1). The aqueous phase is applied to a 1 ml Dowex AG 1×8 ion exchange column. The column is washed with 0.1 N formic acid followed by 0.025 M ammonium formate-0.1 N formic acid. The inositol monophosphate is eluted with 0.2 M ammonium formate-0.1 N formic acid and quantitated by beta counter. In particular, the intrinsic tachykinin receptor antagonist activities of the compounds of the present invention may be demonstrated by these assays. The compounds of the following examples have activity in the aforementioned assays in the range of 0.05 nM to 10 □M. The activity of the present compounds may also be demonstrated by the assay disclosed by Lei, et al., *British J. Pharmacol.*, 105, 261–262 (1992).

With respect to the compounds disclosed in U.S. Pat. Nos. 5,387,595, 5,750,549, 6,479,518 and Bioorg. & Med. Chem. Lett., 1345 (1995), the present compounds exhibit unexpected properties, such as with respect to duration of action and/or metabolism, such as enhanced oral bioavailability or absorption, or decreased drug-drug interactions.

According to a further or alternative aspect, the present invention provides a compound of the present invention for use as a composition that may be administered to a subject in need of a reduction of the amount of tachykinin or substance P in their body.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives.

Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

The compositions containing compounds of the present invention may be presented in unit dosage form and may be prepared by any of the methods well known in the art of pharmacy. The term "unit dosage form" is taken to mean a single dose wherein all active and inactive ingredients are combined in a suitable system, such that the patient or person adminstering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples in the pharmacy arts of unit dosage forms. The compositions containing compounds of the present invention may also be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individuals body in a therapeutically useful form and therapeutically effective amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories. The term "therapeutically effective amount" refers to a sufficient quantity of the compounds of the present invention, in a suitable composition, and in a suitable dosage form to treat or prevent the noted disease conditions.

The compounds of the present invention may be administered in combination with another substance that has a complimentary effect to the tachykinin and substance P inhibitors of the present invention. Accordingly, in the prevention or treatment of emesis, a compound of the present invention may be used in conjunction with other anti-emetic agents, especially $5HT_3$ receptor antagonists, such as ondansetron, granisetron, tropisetron, palenosetron and zatisetron, a corticosteroid, such as dexamethasone, or $GABA_B$ receptor agonists, such as baclofen. Likewise, for the prevention or treatment of migraine a compound of the present invention may be used in conjunction with other anti-migraine agents, such as ergotamines or $5HT_1$ agonists, especially sumatriptan, naratriptan, zolmatriptan or rizatriptan.

It will be appreciated that for the treatment of depression or anxiety, a compound of the present invention may be used in conjunction with other anti-depressant or anti-anxiety agents, such as norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), α-adrenoreceptor antagonists, atypical anti-depressants, benzodiazepines, $5\text{-}HT_{1A}$ agonists or antagonists, especially $5\text{-}HT_{1A}$ partial agonists, corticotropin releasing factor (CRF) antagonists, and pharmaceutically acceptable salts thereof. For the treatment or prevention of eating disorders, including obesity, bulimia nervosa and compulsive eating disorders, a compound of the present invention may be used in conjunction with other anorectic agents. It will be appreciated that for the treatment or prevention of pain or nociception or inflammatory diseases, a compound of the present invention may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent.

It will be appreciated that when using any combination described herein, both the compound of the present invention and the other active agent(s) will be administered to a patient, within a reasonable period of time. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, one active component may be administered as a tablet and then, within a reasonable period of time, the second active component may be administered either as an oral dosage form such as a tablet or a fast-dissolving oral dosage form. By a "fast dissolving oral formulation" is meant, an oral delivery form which when placed on the tongue of a patient, dissolves within about 10 seconds. By "reasonable period of time" is meant a time period that is not in excess of about 1 hour. That is, for example, if the first active component is provided as a tablet, then within one hour, the second active component should be administered, either in the same type of dosage form, or another dosage form which provides effective delivery of the medicament.

The compounds of this invention may be administered to patients (humans and animals, including companion animals, such as dogs, cats and horses) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

In the treatment of the conditions associated with an excess of tachykinins, a suitable dosage level of the compounds of the present invention, or pharmaceutically acceptable salts thereof, is about 0.001 to 50 mg/kg per day, in particular about 0.01 to about 25 mg/kg, such as from about 0.05 to about 10 mg/kg per day. The dosage range will generally be about 0.5 to 1000 mg per patient per day, which may be administered in single or multiple doses. Preferably, the dosage range will be about 0.5 mg to 500 mg per patient per day; more preferably about 0.5 mg to 200 mg per patient per day; and even more preferably about 5 mg to 50 mg per patient per day. Specific dosages of the compounds of the present invention, or pharmaceutically acceptable salts thereof, for administration include 1 mg, 5 mg, 10 mg, 30 mg, 100 mg, and 500 mg. Pharmaceutical compositions of the present invention may be provided in a formulation comprising about 0.5 mg to 1000 mg active ingredient; more preferably comprising about 0.5 mg to 500 mg active ingredient; or 0.5 mg to 250 mg active ingredient; or 1 mg to 100 mg active ingredient. Specific pharmaceutical compositions for treatment or prevention of excess tachykinins comprise about 1 mg, 5 mg, 10 mg, 30 mg, 100 mg and 500 mg of active ingredient.

Several methods for preparing the compounds of this invention are illustrated in the following Examples. Starting materials and the requisite intermediates are in some cases commercially available, or can be prepared according to literature procedures (e.g. U.S. Pat. Nos. 5,387,595, 5,750, 549, 5,877,191, 6,479,518, Bioorg. & Med. Chem. Lett., 1345 (1995), J. Org. Chem., 67, 5993–6000 (2002)) or as illustrated herein. All NMR spectra were obtained on instrumentation at a field strength of 400 or 500 MHz in either $CDCl_3$ or $CD_3OD$ with reported chemical shifts as □. The HPLC/MS analyses were obtained using an Agilent 1100 Series HPLC in combination with a Waters Micromass ZQ mass spectrometer. The HPLC RP column was a Waters Exterra MS-C18 (5 □m) 3.0×50 mm column eluting with a 10–100% acetonitrile/water (both containing 0.05% TFA) gradient over 3.75 min with a run time of 5.50 min. V monitoring was done at 210 nM. Retention times (Rt) are reported in minutes based on the MS data. The reported m/e value was usually the parent molecular ion, except when the 100% ion was not the parent ion as also indicated. Preparative chiral HPLC was done with the indicated Chiracel 25×250 mm columns eluting at 9 mL per min with the indicated percent isopropanol/heptanes solvent mixture. Retention times (Rt) are reported in minutes based on the UV chromatogram monitored at 210 or 254 nm.

Intermediate 1

((1R),(2R),(3S))-3-((1R)-1-(3,5-bis(Trifluoromethyl) phenyl)ethoxy)-2-(4-fluorophenyl)cyclopentane-carboxylic acid Method A: The title compound was prepared as described in U.S. Pat. No. 5,750,549 or was obtained from its ½ TEA salt as described in U.S. Pat. No. 6,479,518 and J. Org. Chem., 67, 5993–6000 (2002). In the latter case, the ½ TEA salt was suspended in water, the water was acidified with 2N HCl until the pH was less than 2, and the mixture was extracted twice with ethyl acetate. The ethyl acetate layers were each successively washed with brine, combined, and dried over sodium sulfate. Removal of solvent in vacuo afforded the free acid as a thick oil which solidified on standing.

Method B: The title compound was also prepared as follows. To a 100 L flask was charged sequentially 113.3 g (0.50 mol) of $Pd(OAc)_2$, 331.4 g (1.11 mol) of 2-(di-t-butylphosphino)biphenyl, 2.476 kg (25.24 mol) of 1,3-cyclopentanedione, and 10.72 kg (50.5 mol) of powdered $K_3PO_4$. The resulting mixture was degassed (3×) by vacuum/$N_2$ back fills. The vessel was then charged with 26 L of 1,4-dioxane and 4.28 kg (32.78 mol) of 1-chloro-4-fluorbenzene and the vessel degassed (3×) with vacuum/$N_2$ back fills. The resulting slurry was heated to reflux for 12 h, cooled to rt, and water (23 L) was added. The vessel was rinsed with an additional 6 L of water and the reaction mixture further diluted with an additional 46 L of water. To the homogeneous solution was added 9 L of conc. HCl to adjust the pH to 1 and the solution aged for 2.5 h. The slurry was then filtered and the cake washed with 17 L of water and 17 L of toluene. The solid was then dried at 60° C. for 48 h, providing 2-(4-fluoro -phenyl)-1,3-cyclopentanedione as a light tan solid.

To a solution of 30.8 mL of THF in a stirred autoclave was added sequentially 17.31 g (81.54 mmol) of $K_3PO_4$, 4.0 g (40.8 mmol) of 1,3-cyclopentanedione, 268 mg (0.989 mmol) of 2-(di-t-butylphosphino)biphenyl, 91.5 mg (0.405 mmol) of $Pd(OAc)_2$, and 6.92 g (53.0 mmol) of 1-chloro-4-fluorobenzene. The sides of the reaction vessel were washed with an additional 10 mL of THF and the vessel purged 3 times with vacuum and nitrogen. The heterogeneous reaction mixture was then heated to 100° C., generating 25 psig pressure in the vessel. The reaction was aged at 100° C. for 12 h, cooled to rt and diluted with 150 mL of water. The resulting homogeneous mixture was distilled to remove THF and then heated to 50° C. The aqueous solution was then slowly acidified using conc. HCl until a final pH of 3 was obtained (10.6 mL). The slurry was cooled to rt and filtered. The wet cake was washed with 40 mL of water, 40 mL of toluene, and dried under vacuum at 60° C. for 24 h to give 2-(4-fluorophenyl)-1,3-cyclopentanedione as a light brown solid.

To a 1-Liter 3-neck flask was charged 50 g (0.26 mol) of 2-(4-fluorophenyl)-1,3-cyclopentanedione as a solid to 260 mL of dry MeCN (KF<100 ug/mL). To the resulting suspension was added 18.5 g (0.13 mol) of $Na_2HPO_4$ and the sides of the reaction flask were washed with an additional 100 ml of dry MeCN. In a separate flask containing 150 mL of MeCN was added 56 g (0.195 mol) of $POBr_3$. The resulting $POBr_3$ solution was then added drop-wise to the slurry, and the mixture was heated to 65° C. for 1.5 h and cooled to rt. The reaction mixture was quenched with 1N KOH to a final pH of <8.0 and aged for 30 min. During the quench the precipitation of insolubles occurs at pH<4 which turns to an oily mass around pH 7–7.5. The bottom oily layer and aqueous layer were separated. The top MeCN layer containing the product was filtered over a small plug of solka floc, which was then rinsed with one bed volume of MeCN. The combined MeCN layers were then concentrated to a final volume of 500 mL. To the concentrated solution was added 600 mL of water at rt and the mixture seeded with 500 mg of 3-bromo-2-(4-fluorophenyl)-2-cyclopenten-1-one. After aging for 30 min, the remaining 700 mL of water were added drop-wise. After 45 min, the slurry was filtered, washed with 100 mL of water and dried under vacuum at 25° C. giving 3-bromo-2-(4-fluorophenyl)-2-cyclopenten-1-one as a light brown solid.

To 50 mL of dry dimethylacetamide (DMAC, KF<100 ug/mL) was added 25 g (98 mmol) of 3-bromo-2-(4-fluorophenyl)-2-cyclopenten-1-one as a solid. In a separate 100 mL round-bottom flask was mixed 2.08 g of 5% Pd/C and 40 mL of DMAC. The slurry containing the catalyst was then added to the flask containing the starting bromide and the 100 mL round bottom flask rinsed with an additional 10 mL DMAC. To the reaction mixture was then added 46.7 mL (196 mmol) of N-tributylamine and 20 mL (473 mmol) of MeOH. The resulting reaction flask was purged with nitrogen (5×) and then with CO (5×). The CO pressure was set at 10 psi and the reaction mixture heated at 60° C. for 12 h. The reaction mixture was filtered over a small plug of solka floc to remove the catalyst and the pad washed with MeOH (172 mL). The methanol was removed under reduced pressure. To the mixture was slowly added 8.6 mL of 1N HCl at such a rate to keep the temperature <24° C., and then the batch was seeded with 1 wt % of methyl 2-(4-fluorophenyl)-3-oxo-1-cyclopent-1-enecarboxylate. After aging for 15 min, 163 mL of 1N HCl was added drop-wise over the next 2.5 hours maintaining the temperature <25° C. The slurry was aged at 15–20° C. for 30 min and sampled for supernatant concentration and filtered. The cake is washed with 17 mL of 1 N HCl and then water until the pH of the filtrate was >5. The product is dried under vacuum/nitrogen sweep for 40 h at 25° C. to give methyl 2-(4-fluorophenyl)-3-oxo-1-cyclopent-1-enecarboxylate as a brown solid.

To 13.2 L of toluene was added 900 mL (0.897 mol) of (R)-2-methyl-oxazaborolidine and 540 mL (5.40 mol) of $BH_3$—$SMe_2$ and the mixture was cooled to −20° C. In a separate round bottom flask was added 2.168 Kg (9.26 mol) of methyl 2-(4-fluorophenyl)-3-oxo-1-cyclopent-1-enecarboxylate and 21 L toluene (final KF~100). The toluene solution of ester was then added drop-wise over 1.25 h at such a rate that the internal temperature did not rise above −20° C. After 1.25 h the reaction mixture was quenched by slow addition of 2.2 liter of MeOH and allowed to warm to rt. The resulting toluene solution was washed with 21 L of 1N HCl, and azeotropically dried (50° C., 25 inHg) to a final volume of 21 liters solution of methyl (3S)-2-(4-fluorophenyl)-3-hydroxycyclopent-1-enecarboxylate.

To a toluene stream containing methyl (3S)-2-(4-fluorophenyl)-3-hydroxycyclopent-1-enecarboxylate in 21 L toluene was added 12 Liters of dry THF and the reaction mixture was cooled to −48° C. To the cooled solution was added drop-wise over 45 min 3.8 Liters (13.46 mol) of 70% Red-Al in toluene. The reaction mixture was allowed to warm to −25° C. over 2.5 h and was added to a solution of 21 L of 2M $NaHSO_4$. The mixture was stirred for 30 min and the layers separated. The toluene layer was then washed with 15 L of water. The toluene layer was then azeotropically dried (50° C., 25 inHg) to a final volume of 21 L (KF 130 ug/mL) and used in the next step. To the toluene solution was added 820 mL (3.6 mol) of 25 wt % NaOMe in MeOH at 50° C. and the mixture heated to 75° C. for 1 h. The mixture was then cooled to 50° C. and 17 L of water, 1 L of MeOH, and 4.5 L of 6N NaOH was added. The mixture was stirred at 20–25° C. overnight. The layers were separated, and the toluene layer discarded. The aqueous layer was then washed with 15 L of MTBE and the MTBE layer discarded. The aqueous layer was then made acidic with conc. HCl (2.1 L, pH 1). The mixture was extracted with 40 L of IPAC. The IPAC layer containing the product (1.35 kg, 69% assay) was then treated with 500 g of Darco for 30 min at 25° C. and filtered over a pad of solka floc, rinsing the pad with and additional 5 L of IPAC. The IPAC solution was then azeotropically dried (45° C., 25 inHg) to a final volume of 15 L (KF<200) and cooled to 20° C. To the IPAC solution was added 3.04 L of n-heptane and the mixture seeded with 5 g of (1R,2R,3S)-2-(4-fluorophenyl)-3-hydroxycyclopentane-1-carboxylic acid. After a good seed bed had been formed (30 min) the rest of the n-heptane (40.4 L) was added drop-wise over 1 hour. The slurry was cooled to 10° C. and filtered. The cake was washed with 2 L of 5:1 n-heptane/IPAC and then with 1 L of heptane. The cake was then dried under vacuum/$N_2$ sweep at 20–25° C. overnight to provide (1R,2R,3S)-2-(4-fluorophenyl)-3-hydroxycyclopentane-1-carboxylic acid as a colorless solid.

A solution of (1R,2R,3S)-2-(4-fluorophenyl)-3-hydroxycyclopentane-1-carboxylic acid (9.8 kg) in methanol (49 L) was heated to reflux in the presence of 10 mol % sulfuric acid. The reaction was complete within 3 h (<2% starting material) and after cooling to 20° C., the resulting solution was diluted with dichloromethane (49 L). This solution was then washed with 0.1M $Na_2HPO_4$ (98 L) followed by saturated $NaCl_{(aq)}$ (49 L). The resulting dichloromethane solution of (1R,2R,3S)-2-(4-fuorophenyl)-3-hydroxycyclopentane-1-carboxylic acid methyl ester was then azeotropically dried with DCM (a further 75 L DCM used) to a final volume of 32 L.

(1R)-1-(3,5-bis(Trifluoromethyl)phenyl)ethanol (15 kg) was dissolved in heptane-dichloromethane (4:1; 150 L) and the resulting solution was then treated with DBU (10 mol %) and trichloroacetonitrile (1.05 equiv.) at 20° C. The addition of $Cl_3CCN$ resulted in a slight exotherm and the temperature of the batch increased gradually to 27° C. After aging at approx. 25° C. for 6 h, the reaction was complete (4% (S)-BTBA). The resulting reaction mixture was washed with 0.1M citric acid (75 L) followed by saturated $NaCl_{(aq)}$ (75 L). A total of <0.5% product was lost to these washes. The resulting organic layer was then concentrated to a final volume of approx. 67 L ((1R)-1-(3,5-bis(trifluoromethyl)phenyl)ethoxy)-trichloroacetimidate in dichloromethane.

The solutions of (1R,2R,3S)-2-(4-fuorophenyl)-3-hydroxycyclopentane-1-carboxylic acid methyl ester in dichloromethane and ((1R)-1-(3,5-bis(trifluoromethyl)phenyl) ethoxy)-trichloro-acetimidate (1.25 equiv.) in heptane, prepared above, were combined and cooled to −8° C. Tetrafluoroboric acid (10 mol %) was added and the batch was left to age at this temperature. Additional $HBF_4$ catalyst (2 mol %) was added and the reaction mixture was left to age at −8° C. overnight. After a total of 23 h, the reaction was determined to be complete by HPLC and was warmed to rt. The resulting slurry was solvent-switched to IPA (final volume of 50 L), 5M $NaOH_{(aq)}$ (3 equiv.) was added and the solution was warmed to 40° C. After 1.5 h, the hydrolysis was complete and the batch was cooled to rt. The resulting solution was diluted with water (100 L) and washed twice with heptane (2×100 L). The aqueous layer was then acidified by addition of conc. hydrochloric acid (3.7 equiv.) and extracted twice with heptane (2×100 L). The combined heptane extracts were then washed twice with water (2×100 L) and concentrated to a volume of 100 L. Negligible product was lost to the heptane washes, the acidified aqueous layer and the combined aqueous washes. To the concentrated heptane solution was added MTBE (10 L) and triethylamine at 45° C. The resulting solution was then allowed to cool to 20° C. overnight during which time the ether-acid TEA salt crystallized from solution. The slurry was therefore cooled to 5° C. before filtering. The filtration liquors contained 1.3% of the desired product ((1R),(2R), (3S))-3-((1R)-1-(3,5-bis(trifluoromethyl)phenyl)ethoxy)-2-(4-fluorophenyl)cyclopentane-carboxylic acid ½ TEA salt. The crude TEA salt (12.96 kg) was dissolved in toluene (100 L) and then washed with 1M HCl (55 L) to remove the triethylamine. The resulting organic layer was then washed with saturated aqueous $NaHCO_3$ (50 L) followed by water (50 L). The resulting toluene solution was concentrated to 20 L and heptane (90 L) was added. The resulting solution was warmed to 50° C., triethylamine (1.1 equiv.) was added and the batch was cooled to 30° C. over 1 h. The slurry that had formed was then allowed to cool to 20° C. overnight. The solid was collected by filtration, washing with 9:1 heptane-toluene (2×20 L) to give ((1R),(2R),(3S))-3-((1R)-1-(3,5-bis(trifluoromethyl)phenyl)ethoxy)-2-(4-fluorophenyl)cyclopentane-carboxylic acid ½ TEA salt. The ½ TEA salt was suspended in water, the water was acidified with 2N HCl until the pH was less than 2, and the mixture was extracted twice with ethyl acetate. The ethyl acetate layers were each successively washed with brine, combined, and dried over sodium sulfate. Removal of solvent in vacuo afforded the free acid as a thick oil which solidified on standing.

EXAMPLE 1

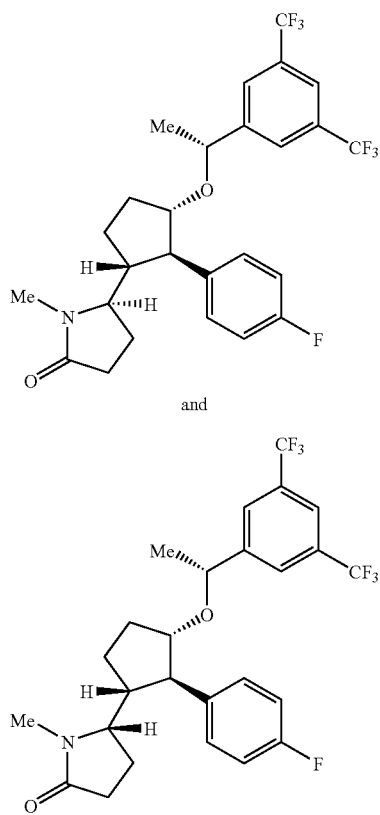

(5R and 5S)-5-(((1R),(2R),(3S))-3-((1R)-1-(3,5-bis(Trifluoromethyl)phenyl)ethoxy)-2-(4-fluorophenyl)cyclopent-1-yl)-1-methylpyrrolidin-2-one Step A: Methyl((1R),(2R),(3S))-3-((1R)-1-(3,5-bis(trifluoromethyl)phenyl)ethoxy)-2-(4-fluorophenyl)cyclopentanecarboxylate Method A: To a solution of ((1R),(2R),(3S))-3-((1R)-1-(3,5-bis(trifluoromethyl)phenyl)ethoxy)-2-(4-fluorophenyl)cyclopentanecarboxylic acid from Intermediate 1 in 1:1 methylene chloride:methanol was added 2M TMS diazomethane in ether until the yellow color persisted. After 5 min, the excess TMS diazomethane was quenched with acetic acid and the volatiles were removed in vacuo to afford the crude title methyl ester. If necessary, purification by FC [flash chromatography] (20–40% ethyl acetate/hexanes) afforded clean title intermediate. HPLC/MS: m/e=479 (M+1), Rt=4.42 min NMR (CDCl$_3$): □ 1.34 (d, 3 H), 1.86–1.92 (m, 1 H), 2.05–2.1 (m, 3 H), 2.80 (q, 1 H), 3.34 (dd, 1 H), 3.78 (q, 1 H), 4.46 (q, 1 H), 6.85–6.95 (m, 2 H), 6.95–7.05 (m, 2 H), 7.44 (s, 2 H), 7.64 (s, 1 H).

Method B: Into a solution of ((1R),(2R),(3S))-3-((1R)-1-(3,5-bis(trifluoromethyl)phenyl)ethoxy)-2-(4-fluorophenyl) cyclopentanecarboxylic acid from Intermediate 1 in methanol was bubbled HCl gas until the solution was saturated. The solution was aged for 16 hr at rt and was then concentrated in vacuo. The residue was diluted with water and extracted twice with ethyl acetate. The ethyl acetate layers were each successively washed with brine containing sodium bicarbonate solution, combined, and dried over sodium sulfate. Removal of solvent in vacuo and purification by FC (20–40% ethyl acetate/hexanes) afforded the title intermediate.

Step B: ((1R),(2R),(3S))-3-((1R)-1-(3,5-bis(Trifluoromethyl)phenyl)ethoxy)-2-(4-fluorophenyl)cyclopentanemethanol Method A: To a solution of methyl ((1R),(2R),(3S))-3-((1R)-1-(3,5-bis(trifluoromethyl)phenyl)-ethoxy)-2-(4-fluorophenyl)cyclopentanecarboxylate (7.6 gm, 15.9 mmol) from Intermediate 1 in THF (150 mL) cooled in an ice bath was added 2M lithium borohydride in THF (16 mL). After 30 min, the reaction was stirred at rt for 16 hr. The reaction was heated to 40° C. for 5 hr, then quenched with 2N HCl solution, diluted with water, and extracted twice with ethyl acetate. The ethyl acetate layers were each successively washed with brine containing sodium bicarbonate solution, combined, and dried over sodium sulfate. Removal of solvent in vacuo and purification by FC (20–40% ethyl acetate/hexanes) afforded the title intermediate alcohol as a clear oil which gradually solidified. Mass spec (NH$_3$/CI): 451(M+1). NMR (CDCl$_3$): □ 1.34 (d, J=6.5 Hz, 3 H), 1.7–1.85 (m, 2 H), 1.85–2.0 (m, 1 H), 2.0–2.15 (m, 2 H), 2.72 (dd, J=8 and 11 Hz, 1 H), 3.52 (dABq, J=6.6 and 10.6 Hz, 2 H), 3.68 (q, J=6 Hz, 1 H), 4.47 (q, J=6.5 Hz, 1 H), 6.85–6.95 (m, 2 H), 6.95–7.05 (m, 2 H), 7.40 (s, 2 H), 7.65 (s, 1 H).

Method B: To a suspension of ((1R),(2R),(3S))-3-((1R)-1-(3,5-bis(trifluoromethyl)phenyl)ethoxy)-2-(4-fluorophenyl)cyclopentanecarboxylic acid ½ TEA salt (25 gm, 48.5 mmol) (see Step A) suspended in toluene (60 mL) and cooled in an ice bath was slowly added 1M borane:THF complex in THF (97 mL). After the initial gas evolution had ceased, the reaction was heated to 75° C. for 1 hr. The reaction was again cooled in an ice bath prior to slow addition of water to quench excess borane. The mixture was diluted with water and extracted twice with ethyl acetate. The ethyl acetate layers were each successively washed with brine containing some sodium bicarbonate solution, combined, dried over sodium sulfate, and concentrated in vacuo. The residue was purified by FC (10–40% ethyl acetate/hexanes) to afford the title intermediate alcohol as a clear oil which gradually solidified. Mass spec (NH$_3$/CI): 451(M+1).

Step C: ((1R),(2R),(3S))-3-((1R)-1-(3,5-bis(Trifluoromethyl)phenyl)ethoxy)-2-(4-fluorophenyl)cyclopentanecarboxaldehyde A solution of oxalyl chloride (1.5 mL) in methylene chloride (40 mL) was cooled in a dry ice/acetone bath and DMSO (2.4 mL) was slowly added. After 15 min, ((1R),(2R),(3S))-3-((1R)-1-(3,5-bis(trifluoromethyl)phenyl)ethoxy)-2-(4-fluorophenyl)cyclopentanemethanol (3.0 gm, 6.7 mmol) from Step B in methylene chloride (10 mL) was added and the reaction was maintained at −70° C. for 1 hr. DIPEA (12 mL) was then added and the reaction was warmed to rt for 2 hr. The reaction was then diluted with water and extracted twice with methylene chloride. The methylene chloride layers were each successively washed with brine containing some sodium bicarbonate solution, combined, dried over sodium sulfate, and concentrated in vacuo. The residue was purified by FC (5% ethyl acetate/hexanes) to afford the title intermediate aldehyde as a clear oil which gradually solidified in the freezer.

Step D: ((1S),(2R),(3R))-1-((1R)-1-(3,5-bis(Trifluoromethyl)phenyl)ethoxy)-2-(4-fluorophenyl)-3-((1R and 1S)-1-hydroxybut-3-en-1-yl)cyclopentane To a solution of ((1R),(2R),(3S))-3-((1R)-1-(3,5-bis(trifluoromethyl)phenyl)ethoxy)-2-(4-fluorophenyl)cyclopentanecarboxaldehyde (1.55 gm, 3.46 mmol) from Step C in THF (20 mL) cooled in an ice bath was added 2M allyl magnesium bromide in THF (2.1 mL). After 30 min TLC still indicated some starting material was left, thus additional 2M allyl magnesium bromide in THF (1 mL) was added. After an additional 90 min at rt, the reaction was quenched into a mixture of water, 2N HCl solution, and ether and the mixture was extracted twice with ether. The ether layers were each successively washed with brine containing some sodium bicarbonate solution, combined, and dried over sodium sulfate. Removal of solvent in vacuo and purification by FC (10–20% ethyl acetate/hexanes) afforded the title intermediate as a mixture of alcohol isomers. HPLC/MS: m/e=-(no ionization), Rt=4.45 min NMR (CDCl$_3$): □ 1.37 (2 d, J=6.5 Hz, 3 H), 1.7–2.25 (4 m, 7 H), 3.00 (m, 1 H), 3.49 (m, 0.5 H), 3.6–3.72 (m 1.5 H), 4.5 (m, 1 H), 4.86–5.1 (m, 2 H), 5.6–5.9 (m, 1 H), 6.93 (2 t, J=8.6 Hz, 2 H), 7.02–7.1 (m, 2 H), 7.45 (s, 2 H), 7.69 (s, 1 H).

Step E: ((1S),(2R),(3R))-1-((1R)-1-(3,5-bis(Trifluoromethyl)phenyl)ethoxy)-2-(4-fluorophenyl)-3-((1R and 1S)-1,4-dihydroxybut-1-yl)cyclopentane To a solution of ((1S),(2R),(3R))-1-((1R)-1-(3,5-bis(trifluoromethyl)phenyl)ethoxy)-2-(4-fluorophenyl)-3-((1R and 1S)-1-hydroxybut-3-en-1-yl)cyclopentane (837 mg, 1.71 mmol) from Step D in THF (8 mL) was added IM borane:THF complex (2.6 mL). After 1 hr at rt, additional 1M borane:THF complex (1 mL) was added. After an additional 1 hr, 5N sodium hydroxide (0.62 mL) and 30% hydrogen peroxide (1.0 mL) were added. The reaction was stirred at rt for 90 min, then quenched into a mixture of water and ether, and extracted twice with ether. The ether layers were each successively washed with brine containing some sodium bicarbonate solution, combined, and dried over sodium sulfate. Removal of solvent in vacuo and purification by Prep TLC (30–50% ethyl acetate/hexanes) afforded the title intermediate as a mixture of hydroxy isomers. HPLC/MS: m/e=509 (M+1), Rt=3.76 min Step F: Methyl 4-(((1R),(2R),(3S))-3-((1R)-1-(3,5-bis(trifluoromethyl)phenyl)ethoxy)-2-(4-fluorophenyl)cyclopent-1-yl)-4-oxobutanoate To a solution of ((1S),(2R),(3R))-1-((1R)-1-(3,5-bis(trifluoromethyl)phenyl)ethoxy)-2-(4-fluorophenyl)-3-((1R and 1S)-1,4-dihydroxybut-1-yl)cyclopentane (710 mg, 1.4 mmol) from Step E in acetone (10 mL) was added 8N Jones reagent (1.6 mL). The reaction was stirred at rt for 30 min and was then concentrated. The residue was diluted with water and extracted twice with ethyl acetate. The ethyl acetate layers were each successively washed with brine, combined, and dried over sodium sulfate. Removal of solvent in vacuo afforded the crude keto-acid which was used directly for the methylation.

To a solution of the above crude acid in 1:1 methylene chloride:methanol (10 mL) was added 2M TMS diazomethane in ether until the yellow color persisted. After 5 min, the excess TMS diazomethane was quenched with acetic acid and the volatiles were removed in vacuo. The residue was purified by prep TLC (20% ethyl acetate/hexanes) to afford the title compound. HPLC/MS: m/e=535 (M+1), Rt=4.37 min NMR (CDCl$_3$): □ 1.37 (d, J=6.4 Hz, 3 H), 1.84 (m, 1 H), 2.02 (m, 1 H), 2.15 (m, 2 H), 2.34–2.7 (m, 4 H), 2.97 (br q, 1 H), 3.31 (dd, J=8.3 and 10.2 Hz, 1 H), 3.64 (s, 3 H), 3.74 (br q, 1 H), 4.5 (q, J=6.4 Hz, 1 H), 6.93 (t, J=8.6 Hz, 2 H), 7.07 (m, 2 H), 7.43 (s, 2 H), 7.69 (s, 1 H).

Step G: (5R and 5S)-5-(((1R),(2R),(3S))-3-((1R)-1-(3,5-bis(Trifluoromethyl)phenyl)ethoxy)-2-(4-fluorophenyl)cyclopent-1-yl)-1-methylpyrrolidin-2-one To a solution of methyl 4-(((1R),(2R),(3S))-3-((1R)-1-(3,5-bis(trifluoromethyl)phenyl)-ethoxy)-2-(4-fluorophenyl)cyclopent-1-yl)-4-oxobutanoate (690 mg, 1.29 mmol) prepared as in Step F in 2M methylamine in methanol (5 mL) was added methylamine hydrochloride (172 mg) and 10% Pd/C (100 mg). The mixture was then hydrogenated on a Parr shaker at 50 p.s.i. for 72 hr. The reaction was filtered, solvent evaporated, fresh 2M methylamine in methanol and Pd/C added, and the hydrogenation continued for another 24 hr. Filtration and evaporation gave a residue which was purified by Prep TLC to afford the title compound as a mixture of lactam isomers. HPLC/MS: m/e=518 (M+1), Rt=4.05 min NMR (CDCl$_3$): □ 1.38 (d, J=6.7 Hz, 3 H), 1.6–2.5 (4m, 9 H), 2.36 and 2.67 (2 s, 3 H), 2.75 and 2.79 (2 dd, J=3.2 and 10 Hz, 1 H), 3.60 (dt, J=4.3 and 8.8 Hz, 1 H), 3.67 and 3.75 (2 q, J=6.6 Hz, 1 H), 4.49 (q, J=6.4 Hz, 1 H), 6.9–7.05 (m, 4 H), 7.43 (s, 2 H), 7.69 (s, 1 H).

EXAMPLE 2

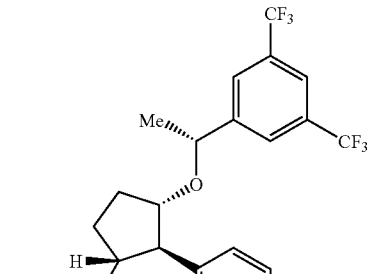

and

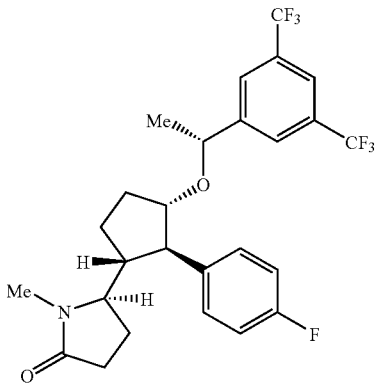

(5R and 5S)-5-(((1R),(2R),(3S))-3-((1R)-1-(3,5-bis(Trifluoromethyl)phenyl)ethoxy)-2-(4-fluorophenyl)cyclopent-1-yl)pyrrolidin-2-one Using essentially the same procedures as in Example 1, Step G, methyl 4-(((1R),(2R),(3S))-3-((1R)-1-(3,5-bis(trifluoromethyl)phenyl)ethoxy)-2-(4-fluorophenyl)cyclopent-1-yl)-4-oxobutanoate (100 mg, 0.187 mmol) from Example 1, Step F in 2M ammonia in methanol (5 mL) and ammonium acetate (14 mg) was hydrogenated on a Parr shaker at 50 p.s.i. for 4 days. The reaction was filtered, solvent evaporated, fresh 2M ammonia in methanol and Pd/C added, and the hydrogenation continued for another 3 days. Filtration and evaporation gave a residue which was purified by Prep TLC to afford recovered starting material (15 mg) and title product as a mixture of (5S) and (5R) lactam isomers. HPLC/MS: m/e=504 (M+1), Rt=3.84 min

EXAMPLE 3

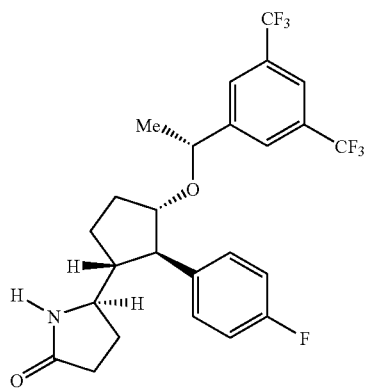

(5R)-5-(((1R),(2R),(3S))-3-((1R)-1-(3,5-bis(Trifluoromethyl)phenyl)ethoxy)-2-(4-fluorophenyl)cyclopent-1-yl)pyrrolidin-2-one Step A: N-Methyl,N-methoxy ((1R),(2R),(3S))-3-((1R)-1-(3,5-bis(trifluoromethyl)phenyl)-ethoxy)-2-(4-fluorophenyl)cyclopentanecarboxamide To a solution of ((1R),(2R),(3S))-3-((1R)-1-(3,5-bis(trifluoromethyl)phenyl)ethoxy)-2-(4-fluorophenyl)cyclopentanecarboxylic acid (10 gm, ~21.4 mmol) from Intermediate 1 (obtained from 11 gm of ½ TEA salt, ~21.4 mmol) in methylene chloride (50 mL) was added at rt DMF (3 drops, cat.) followed by slow addition of oxalyl chloride (2.4 mL, 27 mmol). After stirring at rt for 1 hr, the gas evolution had stopped and the reaction was concentrated to dryness in vacuo. The residue was taken up in methylene chloride and reconcentrated twice to remove excess oxalyl chloride.

The above residue was taken up in methylene chloride (100 mL) and cooled in an ice bath before addition of N,O-dimethylhydroxylamine hydrochloride (2.65 gm, 33 mmol) and then DIPEA (11.6 mL, 65 mmol) over 5 min. The reaction was warmed to rt over 30 min and aged for 2 hr. The reaction was then quenched into a mixture of water and 2N HCl (pH<3) and was extracted twice with methylene chloride. The methylene chloride layers were each successively washed with brine containing some sodium bicarbonate solution, combined, and dried over sodium sulfate. Removal of solvent in vacuo afforded the crude product which was purified by FC (10–40% ethyl acetate/hexanes) to afford the title intermediate (10.8 gm) as a thick oil ($R_f$=0.2 in 20% ethyl acetate/hexanes). HPLC/MS: m/e=508 (M+1), Rt=4.15 min NMR (CDCl$_3$): □ 1.41 (d, J=6.7 Hz, 3 H), 1.9–2.0 (m, 1 H), 2.06 (br q, 2 H), 2.16–2.24 (m, 1 H), 3.12 (s, 3 H), 3.22 (m, 1 H), 3.37 (s, 3 H), 3.53 (dd, J=8.9 and 11 Hz, 1 H), 3.84 (q, J=8.5 Hz, 1 H), 4.55 (q, J=6.7 Hz, 1 H), 6.94 (br t, J=8.7 Hz, 2 H), 7.11 (m, 2 H), 7.49 (s, 2 H), 7.73 (s, 1 H).

Step B: ((1S),(2R),(3R))-1-((1R)-1-(3,5-bis(Trifluoromethyl)phenyl)ethoxy)-2-(4-fluorophenyl)-3-(1-oxopent-4-en-1-yl)cyclopentane To a solution of N-methyl,N-methoxy ((1R),(2R),(3S))-3-((1R)-1-(3,5-bis(trifluoro-methyl)phenyl)ethoxy)-2-(4-fluorophenyl)cyclopentanecarboxamide (5.0 gm, 9.9 mmol) from Step A in THF (50 mL) cooled in an ice bath was added 0.5M but-3-en-1-yl magnesium bromide in THF (25 mL, 12.5 mmol). The reaction was stirred for 30 min and was then allowed to warm to rt. Since TLC (20% ethyl acetate/hexanes) of an aliquot indicated starting material was still present, another 25 mL portion of 0.5M but-3-en-1-yl magnesium bromide in THF was added. After an additional 2 hr, the reaction was quenched into water containing excess 2N HCl and the mixture was extracted twice with ethyl acetate. The ethyl acetate layers were each successively washed with brine containing some sodium bicarbonate solution, combined, and dried over sodium sulfate. Removal of solvent in vacuo afforded the title intermediate (4.8 gm) as a thick oil which can be used directly in the following step ($R_f$=0.75 in 20% ethyl acetate/hexanes) or preferably be purified by FC (10–20% ethyl acetate/hexanes). HPLC/MS: m/e=503 (M+1), Rt=4.53 min NMR (CDCl$_3$): □ 1.40 (d, J=6.6 Hz, 3 H), 1.83–1.92 (m, 1 H), 1.96–2.3 (4 m, 6 H), 2.36–2.44 (m, 1 H), 2.92–3.02 (m, 1 H), 3.33 (dd, J=8.9 and 11 Hz, 1 H), 4.52 (q, J=6.6 Hz, 1 H), 4.92 (m, 1 H), 4.95 (m, 1 H), 5.71 (m, 1 H), 6.96 (br t, J=8.7 Hz, 2 H), 7.08 (m, 2 H), 7.46 (s, 2 H), 7.72 (s, 1 H).

Step C: ((1S),(2R),(3R))-1-((1R)-1-(3,5-bis(Trifluoromethyl)phenyl)ethoxy)-2-(4-fluorophenyl)-3-((1S and 1R)-1-(benzyloxycarbonylamino)pent-4-en-1-yl)cyclopentane (higher (1S) and lower (1R) isomers)

Method A: To a solution of 7N ammonia in methanol (20 mL) was added ((1S),(2R),(3R))-1-((1R)-1-(3,5-bis(trifluoromethyl)phenyl)ethoxy)-2-(4-fluorophenyl)-3-(1-oxopent-4-en-1-yl)cyclopentane (2.0 gm, 4.0 mmol) from Step B and ammonium chloride (350 mg, 6.0 mmol). The reaction flask was sealed with a septum and stirred at rt for 60 min, at which time sodium cyanoborohydride (500 mg, 8.0 mmol) was added portionwise over another 30 min. The reaction was stirred at rt for 16 hr, then quenched into water and sodium hydroxide solution, and extracted twice with methylene chloride. The methylene chloride layers were each successively washed with brine containing some sodium hydroxide solution, combined, and dried over sodium sulfate. Removal of solvent in vacuo afforded the crude amine product as a dark oil. HPLC/MS: m/e=504 (M+1); Rt=3.46 min.

The above residue was taken up in methylene chloride (50 mL) and was cooled in an ice bath. To the solution was added DIPEA (3.6 mL, 20 mmol) and benzyl chloroformate (1.7 mL, 12 mmol). The reaction was allowed to warm to rt over 4 hr and was then quenched into water containing excess 2N HCl. The mixture was extracted twice with methylene chloride and the methylene chloride layers were each successively washed with brine containing some sodium bicarbonate solution, combined, and dried over sodium sulfate. Removal of solvent in vacuo afforded the crude CBZ products as a dark oil. This was purified by FC (5–40% ethyl acetate/hexanes) to afford in order of elution: recovered starting material (360 mg), unknown by-product, higher Rf CBZ (1S) product (430 mg), mixed fractions (200 mg), lower Rf (1R) CBZ product (600 mg), and then two isomeric hydroxyl by-products from reduction of the ketone.

Method B: Method B was done essentially the same as Method A except that only 1 eq. of 7M ammonia in methanol and 10 eq. of ammonium acetate are used in place of excess ammonia and ammonium chloride. The yield of each CBZ isomer is about 40%. (Higher Rf (1S) isomer) HPLC/MS: m/e=638 (M+1), 594 (M+1–44, 100%), Rt=4.70 min (Lower Rf (1R) isomer) HPLC/MS: m/e=638 (M+1), 594 (M+1–44, 100%), Rt=4.70 min NMR (CDCl$_3$): □ 1.39 (d, J=6.7 Hz, 3 H), 1.44–1.5 (m, 1 H), 1.6–1.7 (m, 2 H), 1.74–1.9 (m, 2 H), 1.96–2.04 (m, 2 H), 2.04–2.18 (m, 2 H), 2.83 (dd, J=7.8 and 10.6 Hz, 1 H), 3.65 (m, 1 H), 3.72 (q, J=7.3 Hz, 1 H), 4.48–4.54 (m, 2 H), 4.91 (m, 1 H), 4.93 (m, 1 H), 5.13 (ABq, 2 H), 5.71 (m; 1 H), 6.95 (br t, J=8.7 Hz, 2 H), 7.07 (m, 2 H), 7.35–7.43 (m, 5 H), 7.44 (s, 2 H), 7.71 (s, 1 H).

Step D: (5R)-5-(((1R),(2R),(3S))-3-((1R)-1-(3,5-bis (Trifluoromethyl)phenyl)ethoxy)-2-(4-fluorophenyl) cyclopentan-1-yl)-1-benzyloxycarbonylpyrrolidin-2-one (from lower CBZ (1R) isomer)

Method A: A solution of ((1S),(2R),(3R))-1-((1R)-1-(3,5-bis(trifluoromethyl)phenyl)ethoxy)-2-(4-fluorophenyl)-3-((1R)-1-(benzyloxycarbonylamino)pent-4-en-1-yl)cyclopentane (lower (1R) isomer from Step C) (600 mg, 0.94 mmol) in methanol (30 mL) was cooled in a dry ice/acetone bath to –70° C. Ozone was bubbled into the solution until the blue color presisted. Excess ozone was remove with a stream of nitrogen and the ozonide mixture was quenched with dimethyl sulfide (5 mL). The mixture was allowed to warm to rt for 2 hr and 2 drops of 2N HCl were added prior to concentration of the reaction in vacuo. The residue was taken up in acetone (25 mL) and evaporated to remove water. The residue was again taken up in acetone (25 mL) and excess Jones reagent (0.50 mL) was added at rt all at once. After stirring for 2 hr, the reaction was quenched into water and the mixture was extracted twice with ethyl acetate. The ethyl acetate layers were each successively washed with brine containing some sodium bicarbonate solution, combined, and dried over sodium sulfate. Removal of solvent in vacuo and purification by FC (20–40% ethyl acetate/hexanes) afforded the title intermediate.

Method B: Method B was done essentially the same as Method A except that on larger scale the crude ozonolysis product in acetone was slowly added to excess Jones Reagent in acetone at less than 30° C. After 1 hr, the excess Jones Reagent was quenched with isopropanol. Work-up and purification was done as in Method A. HPLC/MS: m/e=638 (M+1), 594 (M+1–44, 100%), Rt=4.35 min NMR (CDCl$_3$): □ 1.34 (d, J=6.5 Hz, 3 H), 1.62–1.8 (m, 2 H), 1.8–1.9 (m, 2 H), 2.0–2.1 (m, 2 H), 2.36–2.58 (m, 2 H), 2.68–2.8 (m, 2 H), 3.52 (q, J=6.2 Hz, 1 H), 4.35 (ddd, 1 H), 4.41 (q, J=6.5 Hz, 1 H), 5.06 (ABq, J=12.4 Hz, 2 H), 6.77 (br t, J=8.6 Hz, 2 H), 6.90 (m, 2 H), 7.15–7.35 (m, 5 H), 7.35 (s, 2 H), 7.64 (s, 1 H).

Step E: (5R)-5-(((1R),(2R),(3S))-1-((1R)-1-(3,5-bis (Trifluoromethyl)phenyl)ethoxy)-2-(4-fluorophenyl) cyclopentan-1-yl)pyrrolidin-2-one (lower (R) isomer)

A solution of (5R)-5-(((1R),(2R),(3S))-1-((1R)-1-(3,5-bis (trifluoromethyl)phenyl)-ethoxy)-2-(4-fluorophenyl)cyclopentan-1-yl)-1-benzyloxycarbonylpyrrolidin-2-one (lower (R) isomer from Step D) (400 mg, 0.63 mmol) in methanol (5 mL) was hydrogenated on a Parr shaker at 50 p.s.i. for 1 hr when TLC indicated the reaction was complete. The reaction was filtered and evaporated. The residue was purified on 6×1000 □M prep plates (3% methanol in methylene chloride) to remove any residual higher Rf isomer and afforded pure title compound. HPLC/MS: m/e=504 (M+1), Rt=3.85 min NMR (CDCl$_3$): □ 1.38 (d, J=6.6 Hz, 3 H), 1.4–1.53 (m, 1 H), 1.68–1.88 (m, 2 H), 1.88–2.0 (m, 2 H), 2.0–2.15 (m, 2 H), 2.2–2.26 (m, 2 H), 2.69 (dd, J=7.2 and 10.1 Hz, 1 H), 3.61 (q, J=6.9 Hz, 1 H), 3.66 (q, J=5.9 Hz, 1 H), 4.49 (q, J=6.6 Hz, 1 H), 6.16 (s, 1 H), 6.95 (br t, J=8.6 Hz, 2 H), 7.01 (m, 2 H), 7.42 (s, 2 H), 7.69 (s, 1 H).

EXAMPLE 4

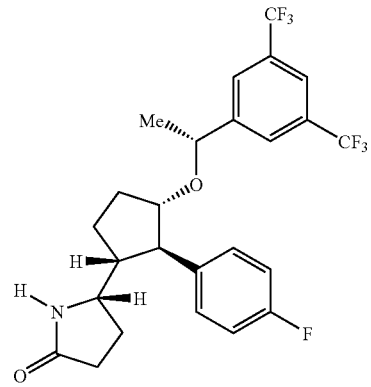

(5S)-5-(((1R),(2R),(3S))-3-((1R)-1-(3,5-bis(Trifluoromethyl)phenyl)ethoxy)-2-(4-fluorophenyl)cyclopentan-1-yl)pyrrolidin-2-one Using essentially the same procedures as in Example 3, Step D–E, ((1S),(2R),(3R))-1-((1R)-1-(3,5-bis(trifluoromethyl)phenyl)ethoxy)-2-(4-fluorophenyl)-3-((1S)-1-(benzyloxycarbonyl-amino)pent-4-en-1-yl)cyclopentane (higher (1S) isomer from Example 3, Step C) (60 mg, 0.094 mmol) was converted to the title compound. HPLC/MS: m/e=504 (M+1), Rt=3.95 min NMR (CDCl$_3$): □ 1.37 (d, J=6.4 Hz, 3 H), 1.56–1.68 (m, 1 H), 1.68–1.86 (m, 2 H), 1.86–1.98 (m, 2 H), 1.98–2.16 (m, 2 H), 2.2–2.26 (m, 2 H), 2.74 (dd, J=7.8 and 10.5 Hz, 1 H), 3.58 (q, J=7.2 Hz, 1 H), 3.66 (q, J=5.9 Hz, 1 H), 4.47 (q, J=6.6 Hz, 1 H), 5.08 (s, 1 H), 6.97 (br t, J=8.6 Hz, 2 H), 7.05 (m, 2 H), 7.42 (s, 2 H), 7.69 (s, 1 H).

EXAMPLE 6

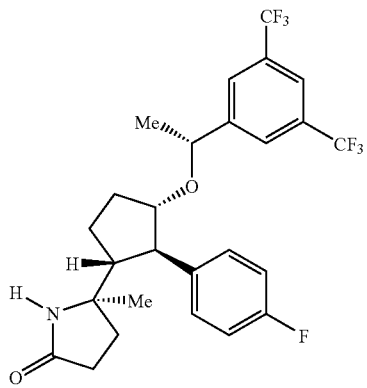

(5R)-5-(((1R),(2R),(3S))-3-((1R)-1-(3,5-bis(Trifluoromethyl)phenyl)ethoxy)-2-(4fluorophenyl)-cyclopentan-1-yl)-5-methylpyrrolidin-2-one Step A: ((1S),(2R),(3R))-1-((1R)-1-(3,5-bis(Trifluoromethyl)phenyl)ethoxy)-2-(4-fluorophenyl)-3-((2R and 2S)-2-hydroxyhex-5-en-2-yl)cyclopentane To a solution of ((1S),(2R),(3R))-1-((1R)-1-(3,5-bis(trifluoromethyl)phenyl)ethoxy)-2-(4-fluorophenyl)-3-(1-oxopent-4-en-1-yl)cyclopentane (5.0 gm, 10 mmol) prepared as in Example 3, Step B, in THF (50 mL) was added at rt 1.4M methyl magnesium bromide (10.7 mL). After 1 hr, additional Grignard (5 mL) was added and the reaction was stirred for another hr. The reaction was then quenched into water containing excess 2N HCl and the mixture was extracted twice with ethyl acetate. The ethyl acetate layers were each successively washed with brine containing some sodium bicarbonate solution, combined, and dried over sodium sulfate. Removal of solvent in vacuo and purification by FC (10–30% ethyl acetate/hexanes) afforded partial separation of both title isomeric intermediates (5.15 gm). NMR (CDCl$_3$) (Higher Rf): □ 1.05 (s, 3 H), 1.38 (d, J=6.6 Hz, 3 H), 1.46 (t, J=7.8 Hz, 2 H), 1.72–1.82 (m, 1 H), 1.82–2.06 (m, 5 H), 2.24 (q, J=7.6 Hz, 1 H), 3.12 (dd, J=6.7 and 9.0 Hz, 1 H), 3.55 (q, J=6.3 Hz, 1 H), 4.51 (q, J=6.6 Hz, 1 H), 4.88–4.95 (m, 2 H), 5.73 (tdd, 1 H), 6.93 (br t, J=8.6 Hz, 2 H), 7.04–7.09 (m, 2 H), 7.45 (s, 2 H), 7.69 (s, 1 H). NMR (CDCl$_3$) (Lower Rf): □ 1.15 (s, 3 H), 1.38 (d, J=6.6 Hz, 3 H), 1.45 (tABq, 2 H), 1.74–1.90 (m, 4 H), 1.96–2.06 (m, 2 H), 2.23 (q, J=7.6 Hz, 1 H), 3.12 (dd, J=6.4 and 9.0 Hz, 1 H), 3.57 (q, J=6.0 Hz, 1 H), 4.51 (q, J=6.6 Hz, 1 H,) 4.81–4.87 (3 m, 2 H), 5.59–5.70 (m, 1 H), 6.93 (br t, J=8.6 Hz, 2 H), 7.06–7.11 (m, 2 H), 7.46 (s, 2 H), 7.70 (s, 1 H).

Step B: ((1S),(2R),(3R))-1-((1R)-1-(3,5-bis(Trifluoromethyl)phenyl)ethoxy)-2-(4-fluorophenyl)-3-((2R and 2S)-2-(acetylamino)hex-5-en-2-yl)cyclopentane To a solution of ((1S),(2R),(3R))-1-((1R)-1-(3,5-bis(trifluoromethyl)phenyl)ethoxy)-2-(4-fluorophenyl)-3-((2R and 2S)-2-hydroxyhex-5-en-2-yl)cyclopentane (5.1 gm, 9.8 mmol) from Step A (mix fractions) in acetonitrile (150 mL) at rt was added conc. sulfuric acid (5 mL). After 2 hr, the reaction was quenched into sodium bicarbonate solution and was extracted twice with ethyl acetate. The ethyl acetate layers were each successively washed with brine containing some sodium bicarbonate solution, combined, and dried over sodium sulfate. Removal of solvent in vacuo and purification by FC (10–40% ethyl acetate/hexanes) separated a major non-polar by-product, a trace of starting material, followed by the higher Rf (2S) title intermediate (700 mg) and lower Rf (2R) title intermediate (800 mg) (Rf=0.15 and 0.25 in 30% ethyl acetate/hexanes). HPLC/MS: m/e=560 (M+1), Rt=4.37 min NMR (CDCl$_3$) (Higher Rf): □ 1.28 (s, 3 H), 1.39 (d, J=6.5 Hz, 3 H), 1.39 (s, 3 H), 1.56–1.66 (m, 1 H), 1.66–1.95 (m, 5 H), 1.97–2.08 (m, 1 H), 2.12–2.21 (m, 1 H), 2.77 (q, J=7.6 Hz, 1 H), 2.97 (dd, J=6.7 and 9.0 Hz, 1 H), 3.59 (q, J=6.3 Hz, 1 H), 4.49 (q, J=6.6 Hz, 1 H), 4.84–4.91 (3 m, 2 H), 5.25 (s, 1 H), 5.71 (tdd, 1 H), 6.95 (br t, J=8.6 Hz, 2 H), 7.04–7.09 (m, 2 H), 7.44 (s, 2 H), 7.70 (s, 1 H). HPLC/MS: m/e=560 (M+1), Rt=4.37 min NMR (CDCl$_3$) (Lower Rf): □ 1.31 (s, 3 H), 1.40 (d, J=6.6 Hz, 3 H), 1.45 (m, 1 H), 1.67 (s, 3 H), 1.72–1.83 (m, 2 H), 1.83–2.04 (m, 5 H), 2.86–2.97 (m, 2 H), 3.57 (q, J=6.0 Hz, 1 H), 4.51 (q, J=6.6 Hz, 1 H), 4.88–4.95 (3 m, 2 H), 5.24 (br s, 1 H), 6.93 (br t, J=8.6 Hz, 2 H), 7.03–7.08 (m, 2 H), 7.47 (s, 2 H), 7.70 (s, 1 H).

Step C: N-Acetyl (5R)-5-(((1R),(2R),(3S))-3-((1R)-1-(3,5-bis(Trifluoromethyl)phenyl)-2-(4-fluorophenyl)cyclopentan-1-yl)-5-methylpyrrolidin-2-one Using essentially the same procedure as in Example 3, Step D, but using the lower Rf ((1S),(2R),(3R))-1-((1R)-1-(3,5-bis(trifluoromethyl)phenyl)ethoxy)-2-(4-fluorophenyl)-3-((2R)-2-(acetylamino)hex-5-en-2-yl)cyclopentane (800 mg, 1.4 mmol) from Step B, the title intermediate was obtained after FC (15–30% ethyl acetate/hexanes). HPLC/MS: m/e=560 (M+1), Rt=4.32 min NMR (CDCl$_3$): □ 1.38 (d, J=6.7 Hz, 3 H), 1.55 (s, 3 H), 1.73 (s, 3 H), 1.65–1.84 (m, 3 H), 1.91–1.99 (m, 1 H), 2.05–2.15 (m, 1 H), 2.35–2.42 (m, 1 H), 2.55–2.61 (m, 2 H), 2.71 (dd, J=7.1 and 11 Hz, 1 H), 3.39 (q, J=10.5 Hz, 1 H), 3.57 (q, J=6.4 Hz, 1 H), 4.51 (q, J=6.6 Hz, 1 H), 6.88–6.96 (m, 4 H), 7.39 (s, 2 H), 7.70 (s, 1 H).

Step D: (5R)-5-(((1R),(2R),(3S))-3-((1R)-1-(3,5-bis(Trifluoromethyl)phenyl)ethoxy)-2-(4-fluorophenyl)cyclopentan-1-yl)-5-methylpyrrolidin-2-one To a solution of N-acetyl (5R)-5-(((1R),(2R),(3S))-3-((1R)-1-(3,5-bis(trifluoromethyl)-phenyl)ethoxy)-2-(4-fluorophenyl)cyclopentan-1-yl)-5-methylpyrrolidin-2-one (330 mg, 0.59 mmol) from Step C in isopropanol (20 mL) was added hydrazine (0.20 mL). After stirring for 24 hr at rt, additional hydrazine (0.10 mL) was added and the mixture was heated to 60° C. for 4 hr. The reaction was then concentrated in vacuo and the residue was diluted with water, acidified with 2N HCl, and extracted twice with ethyl acetate. The ethyl acetate layers were each successively washed with brine containing some sodium bicarbonate solution, combined, and dried over sodium sulfate. Removal of solvent in vacuo and purification by FC (40–75% ethyl acetate/hexanes, then 5% methanol/ethyl acetate) afforded the title product. HPLC/MS: m/e=518 (M+1), Rt=3.97 min NMR (CDCl$_3$): □ 1.22 (s, 3 H), 1.39 (d, J=6.6 Hz, 3 H), 1.58–1.66 (m, 1 H), 1.71–1.96 (m, 4 H), 2.03–2.13 (m, 1 H), 2.21–2.30 (m, 2 H), 2.21–2.41(m, 1 H), 2.81 (dd, J=6.8 and 9.4 Hz, 1 H), 3.61 (q, J=6.2 Hz, 1 H), 4.50 (q, J=6.4 Hz, 1 H), 6.20 (s, 1 H), 6.94 (br t, J=8.5 Hz, 2 H), 7.03–7.08 (m, 2 H), 7.44 (s, 2 H), 7.70 (s, 1 H).

EXAMPLE 7

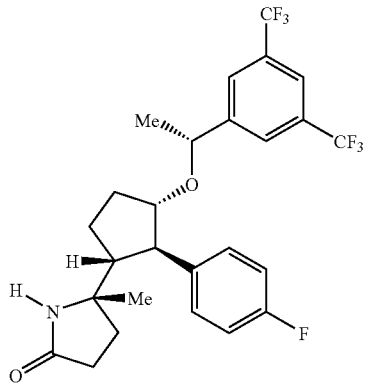

(5S)-5-(((1R),(2R),(3S))-3-((1R)-1-(3,5-bis(Trifluoromethyl)phenyl)ethoxy)-2-(4fluorophenyl)cyclopentan-1-yl)-5-methylpyrrolidin-2-one Using essentially the same procedure as in Example 6, Steps C–D, but using the higher Rf ((1S),(2R),(3R))-1-((1R)-1-(3,5-bis(trifluoromethyl)phenyl)ethoxy)-2-(4-fluorophenyl)-3-((2S)-2-(acetylamino)hex-5-en-2-yl)cyclopentane (5.8 g) prepared as in Example 6, Step B, the title product was obtained after column chromatography (2% methanol/methylene chloride). HPLC/MS: m/e=518 (M+1), Rt=3.99 min

EXAMPLE 8

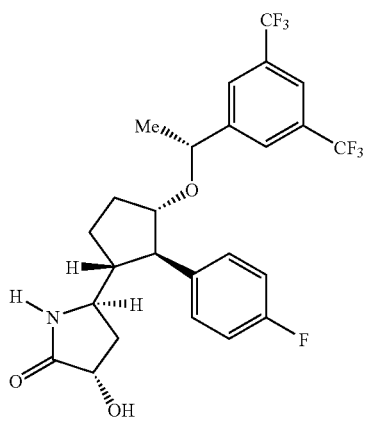

Faster, major
and

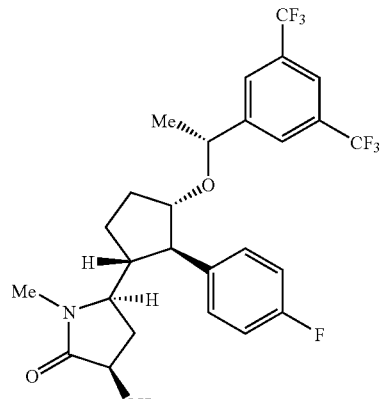

Slower, minor (3R,5R and 3S,5R)-5-(((1R),(2R),(3S))-3-((1R)-1-(3,5-bis(Trifluoromethyl)phenyl)ethoxy)-2-(4-fluorophenyl)cyclopentan-1-yl)-3-hydroxypyrrolidin-2-one Step A: (3R,5R and 3S,5R)-5-(((1R),(2R),(3S))-3-((1R)-1-(3,5-bis(Trifluoromethyl)phenyl)-ethoxy)-2-(4-fluorophenyl)cyclopentan-1-yl)-1-benzyloxycarbonyl-3-hydroxypyrrolidin-2-one To a solution of (5R)-5-(((1R),(2R),(3S))-3-((1R)-1-(3,5-bis(trifluoromethyl)phenyl)-ethoxy)-2-(4-fluorophenyl)cyclopentan-1-yl)-1-benzyloxycarbonylpyrrolidin-2-one (0.91 gm, 1.43 mmol prepared as in Example 3, Step D (from lower (1R) CBZ isomer of Step C) in THF (40 mL) was cooled to −70° C. and 1M LiHMDS (2.1 mL) was added. After 10 min, the mixture was allowed to warm to −20° C. for 30 min after which time solid, dried MoOPH reagent (1.24 gm) was added. The reaction was stirred at rt for 40 min before being quenched with an aq. solution of sodium sulfite and 2N HCl. The mixture was diluted with water and extracted twice with ethyl acetate. The ethyl acetate layers were each successively washed with brine containing some sodium bicarbonate solution, combined, and dried over sodium sulfate. Removal of solvent in vacuo and purification by FC (30–40% ethyl acetate/hexanes) afforded the title intermediate as a mixture of isomers. HPLC/MS: m/e=610 (M+1−44, 100%), 654 (M+1), Rt=4.18 min Step B: (3R,5R and 3S,5R)-5-(((1R),(2R),(3S))-3-((1R)-1-(3,5-bis(Trifluoromethyl)phenyl)-ethoxy)-2-(4-fluorophenyl)cyclopentan-1-yl)-3-hydroxypyrrolidin-2-one A solution of (3R,5R and 3S,5R)-5-(((1R),(2R),(3S))-3-((1R)-1-(3,5-bis(trifluoromethyl)phenyl)ethoxy)-2-(4-fluorophenyl)cyclopentan-1-yl)-1-benzyloxycarbonyl-3-hydroxypyrrolidin-2-one (320 mg) from Step A was hydrogenated as in Example 3, Step E, to afford the title product (225 mg) as a mixture of hydroxy isomers. Some of this mixture was then separated using a preparative Chiracel OD column eluting with 15% isopropanol/heptanes to afford the major, faster (3S,5R) isomer and minor, slower (3R,5R)

isomer. Faster product; HPLC/MS: m/e=520 (M+1), Rt=3.72 min. NMR (CDCl₃): □ 1.39 (d, J=6.6 Hz, 3 H), 1.63–1.72 (m, 1 H), 1.78–1.87 (m, 1 H), 1.87–1.98 (m, 2 H), 1.98–2.06 (m, 2 H), 2.06–2.15 (m, 1 H), 2.70 (dd, J=7.4 and 10.4 Hz, 1 H), 3.62–3.71 (m, 2 H), 4.23 (t, J=7.3 Hz, 1 H), 4.50 (q, J=6.4 Hz, 1 H), 6.51 (s, 1 H), 6.97 (br t, J=8.5 Hz, 2 H), 7.03–7.08 (m, 2 H), 7.44 (s, 2 H), 7.70 (s, 1 H). Slower product; HPLC/MS: m/e=520 (M+1), Rt=3.73 min. NMR (CDCl₃): □ 1.38 (d, J=6.6 Hz, 3 H), 1.71–1.88 (m, 2 H), 1.88–2.04 (m, 2 H), 2.04–2.15 (m, 2 H), 2.26–2.34 (m, 1 H), 2.81 (dd, J=7.3 and 10 Hz, 1 H), 3.53 (m, 1 H), 3.59 (q, J=8.9 Hz, 1 H), 4.25 (t, J=9.1 Hz, 1 H), 4.52 (q, J=6.4 Hz, 1 H), 6.97 (br t, J=8.5 Hz, 2 H), 7.03–7.08 (m, 2 H), 7.44 (s, 1 H), 7.46 (s, 2 H), 7.72 (s, 1 H).

EXAMPLE 9

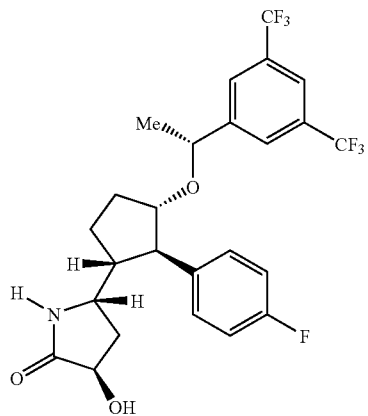

Faster, major and

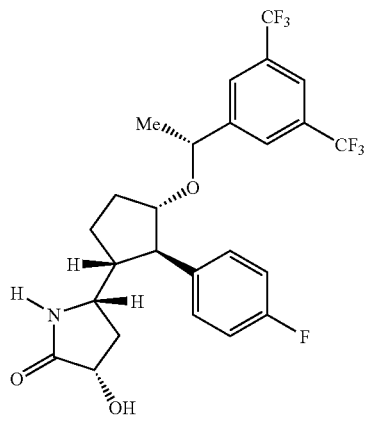

Slower, minor (3R,5S and 3S,5S)-5-(((1R),(2R),(3S))-3-((1R)-1-(3,5-bis(Trifluoromethyl)phenyl)ethoxy)2-(4-fluorophenyl)cyclopentan-1-yl)-3-(hydroxy)pyrrolidin-2-one Using essentially the same procedures as in Example 8, but starting with (5S)-5-(((1R),(2R),(3S))-3-((1R)-1-(3,5-bis(trifluoromethyl)phenyl)ethoxy)-2-(4-fluorophenyl)cyclopentan-1-yl)-1-benzyloxycarbonylpyrrolidin-2-one (1.3 gm, 2.0 mmol) prepared as in Example 4 (from higher (1S) CBZ isomer of Example 3, Step C), the title compounds were prepared as a mixture. The isomers can be separated as the CBZ derivative by FC (30–60% ethyl acetate/hexanes) or as the title compounds using a preparative Chiracel OD column (10% isopropanol/heptanes) to afford the major, faster (3R,5S) isomer (Rt=26 min) and minor, slower (3S, 5S) isomer (Rt=32 min). HPLC/MS (Faster): m/e=520 (M+1), Rt=3.73 min HPLC/MS (Slower): m/e=520 (M+1), Rt=3.73 min

EXAMPLE 10

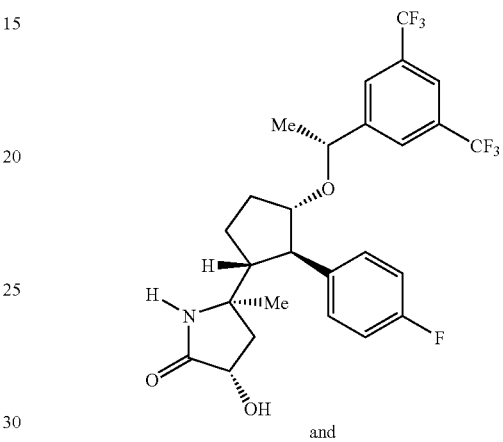

and

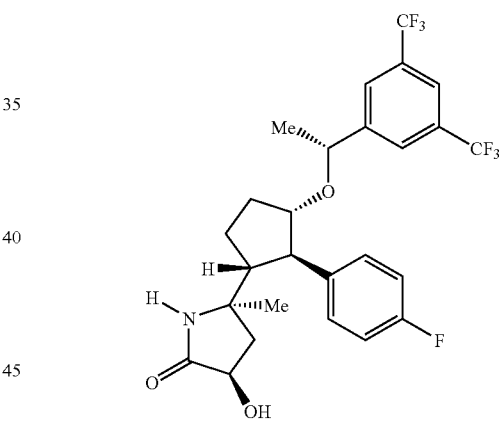

(3R,5R and 3S,5R)-5-(((1R),(2R),(3S))-3-((1R)-1-(3,5-bis(Trifluoromethyl)phenyl)ethoxy)-2-(4-fluorophenyl)cyclopentan-1-yl)-3-hydroxy-5-methylpyrrolidin-2-one Step A: (5R)-5-(((1R),(2R),(3S))-3-((1R)-1-(3,5-bis(Trifluoromethyl)phenyl)ethoxy)-2-(4-fluorophenyl)cyclopentan-1-yl)-1-benzyloxycarbonyl-5-methylpyrrolidin-2-one To a solution of (5R)-5-(((1R),(2R),(3S))-3-((1R)-1-(3,5-bis(trifluoromethyl)phenyl)-ethoxy)-2-(4-fluorophenyl)cyclopentan-1-yl)-5-methylpyrrolidin-2-one (1.0 gm, 1.9 mmol) prepared as Example 6, Step D (from lower (1R) acetylamino isomer of Step C) in THF (10 mL) was cooled to −70° C. and 1M LiHMDS (3.8 mL) was added. After 30 min, benzyl chloroformate (0.552 mL) was added and the reaction was allowed to warm to rt for 1 hr. The mixture was quenched into water and aq. 2N HCl and extracted twice with ethyl acetate. The ethyl acetate layers were each successively washed with brine containing some sodium bicarbonate solution, combined, and dried over sodium sulfate. Removal of solvent in vacuo and purification by FC (10–30% ethyl acetate/hexanes) afforded the title intermediate and recovered starting material. HPLC/MS: m/e=608 (M+1–44, 100%), 652 (M+1); Rt=4.48 min Step B: (3R,5R and 3S,5R)-5-(((1R),(2R),(3S))-3-((1R)-1-(3,5-bis(Trifluoromethyl)-phenyl)ethoxy)-2-(4-fluorophenyl)cyclopentan-1-yl)-1-benzyloxycarbonyl-3-hydroxy-5-methylpyrrolidin-2-one To a solution of (5R)-5-(((1R),(2R),(3S))-3-((1R)-1-(3,5-bis(trifluoromethyl)phenyl)-ethoxy)-2-(4-fluorophenyl)cyclopentan-1-yl)-1-benzyloxycarbonyl-5-methylpyrrolidin-2-one (0.535 gm, 0.85 mmol) prepared in Step A in THF (20 mL) was cooled to −70° C. and 1M LiHMDS in THF (1.0 mL) was added. After 10 min, the mixture was allowed to warm to −20° C. for 30 min after which time solid MoOPH reagent (740 mg) was added. The reaction was stirred at rt for 40 min before being quenched with an aq. solution of sodium sulfite and 2N HCl. The mixture was diluted with water and extracted twice with ethyl acetate. The ethyl acetate layers were each successively washed with brine containing some sodium bicarbonate solution, combined, and dried over sodium sulfate. Removal of solvent in vacuo and purification by FC (20–40% ethyl acetate/hexanes) afforded recovered starting material and the title intermediate as a mixture of isomers. HPLC/MS: m/e=624 (M+1–44, 100%), 668 (M+1); Rt=4.26 min Step C: (3R,5R and 3S,5R)-5-(((1R),(2R),(3S))-3-((1R)-1-(3,5-bis(Trifluoromethyl)phenyl)-ethoxy)-2-(4-fluorophenyl)cyclopentan-1-yl)-3-hydroxy-5-methylpyrrolidin-2-on A solution of (3R,5R and 3S,5R)-5-(((1R),(2R),(3S))-3-((1R)-1-(3,5-bis(trifluoromethyl)-phenyl)ethoxy)-2-(4-fluorophenyl)cyclopentan-1-yl)-1-benzyloxycarbonyl-3-hydroxy-5-methylpyrrol-idin-2-one (300 mg) from Step B was hydrogenated as in Example 3, Step E, to afford the title product (226 mg) as a mixture of hydroxy isomers. The isomers were then separated using a preparative Chiracel OD column eluting with 10% isopropanoUheptanes to afford the faster, minor (3R,5R) isomer and slower, major (3S,5R) isomer. HPLC/MS (Faster, minor): m/e=534 (M+1), Rt=4.13 min. NMR (CDCl3): □ 1.26 (s, 3 H), 1.41 (d, J=6.4 Hz, 3 H), 1.74–186 (m, 2 H), 1.86–1.97 (m, 2 H), 2.20–2.11 (m, 1 H), 2.12–2.18 (m, 1 H), 2.30 (q, J=8.7 Hz, 1 H), 2.94 (dd, J=6.4 and 9.2 Hz, 1 H), 3.61 (q, J=5.7 Hz, 1 H), 4.40 (t, J=7.6 Hz, 1 H), 4.52 (q, J=6.4 Hz, 1 H), 5.83 (br s, 1 H), 6.96 (br t, J=8.7 Hz, 2 H), 7.02–7.07 (m, 2 H), 7.47 (s, 2 H), 7.72 (s, 1 H). HPLC/MS (Slower, major): m/e=534 (M+1), Rt=4.08 min. NMR (CDCl3): □ 1.31 (s, 3 H), 1.41 (d, J=6.6 Hz, 3 H), 1.67 (dd, J=7.1 and 13.7, 1 H), 1.66–1.76 (m, 1 H), 1.76–1.86 (m, 1 H), 1.87–1.96 (m, 1 H), 2.08 (hex, 1 H), 2.23 (q, J=9.8 Hz, 1 H), 2.19 (dd, J=7.1 and 13.7 Hz, 1 H), 2.76 (dd, J=6.8 and 9.9 Hz, 1 H), 3.61 (q, J=6.2 Hz, 1 H), 4.30 (dd, J=7.4 and 8.5 Hz, 1 H), 4.50 (q, J=6.6 Hz, 1 H), 6.16 (br s, 1 H), 6.96 (br t, J=8.7 Hz, 2 H), 7.02–7.07 (m, 2 H), 7.44 (s, 2 H), 7.72 (s, 1 H).

EXAMPLE 11

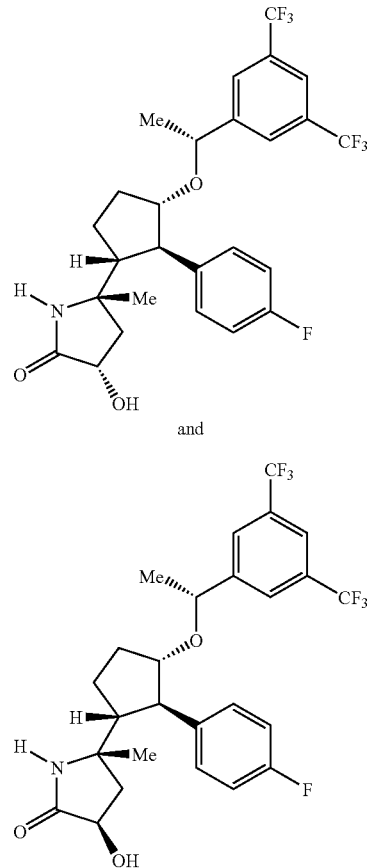

(3R,5S and 3S,5S)-5-(((1R),(2R),(3S))-3-((1R)-1-(3,5-bis(Trifluoromethyl)phenyl)ethoxy)_2-(4-fluorophenyl)cyclopentan-1-yl)-3-hydroxy-5-methylpyrrolidin-2-one Using essentially the same procedures as in Example 10, but starting with (5S)-5-(((1R),(2R),(3S))-3-((1R)-1-(3,5-bis(trifluoromethyl)phenyl)ethoxy)-2-(4-fluorophenyl)cyclopentan-1-yl)-1-benzyloxycarbonyl-5-methylpyrrolidin-2-one (1.0 gm, 1.9 mmol) prepared as in Example 7 (from higher (1S) acetyl isomer of Example 6, Step B), the title compounds were prepared as a mixture. The isomers were separated using a preparative Chiracel OD column (15% isopropanol/heptanes) to afford the major, faster (3S,5S) isomer and minor, slower (3S,5R) isomer. Faster product; HPLC/MS: m/e=534 (M+1), Rt=3.78 min. NMR (CDCl3): □ 1.32 (s, 3 H), 1.40 (d, J=6.7 Hz, 3 H), 1.64–1.74 (m, 1 H), 1.77 (dd, J=7.1 and 13.5, 1 H), 1.74–1.83 (m, 1 H), 1.91–2.00 (m, 1 H), 2.07 (hex, 1 H), 2.23 (q, J=9.8 Hz, 1 H), 2.37 (dd, J=7.1 and 13.5 Hz, 1 H), 2.84 (dd, J=7.4 and 10.3 Hz, 1 H), 3.59 (q, J=6.2 Hz, 1 H), 4.27 (dd, J=7.4 and 8.5 Hz, 1 H), 4.48 (q, J=6.6 Hz, 1 H), 5.62 (br s, 1 H), 6.98 (br t, J=8.7 Hz, 2 H), 7.05–7.10 (m, 2 H), 7.43 (s, 2 H), 7.71 (s, 1 H). Slower product; HPLC/MS: m/e=534 (M+1), Rt=3.80 min.

EXAMPLE 12

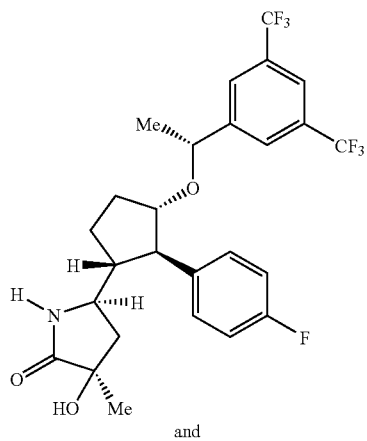

and

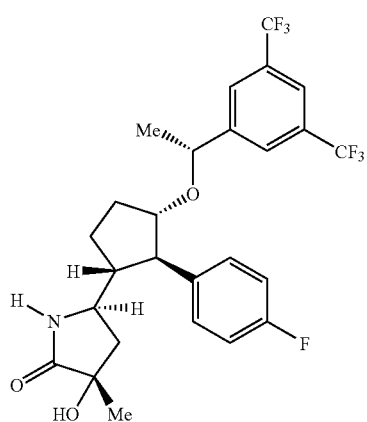

(3R,5R and 3S,5R)-5-(((1R),(2R),(3S))-3-((1R)-1-(3,5-bis(Trifluoromethyl(phenyl)ethoxy)-2-(4-fluorophenyl)cyclopentan-1-yl)-3-hydroxy-3-methylpyrrolidin-2-one Step A: (5R)-5-(((1R),(2R),(3S))-3-((1R)-1-(3,5-bis(Trifluoromethyl)phenyl)ethoxy)-2-(4-fluorophenyl)cyclopentan-1-yl)-3-oxoypyrrolidin-2-one To a solution of (3R,5R and 3S,5R)-5-(((1R),(2R),(3S))-3-((1R)-1-(3,5-bis(trifluoro-methyl)phenyl)ethoxy)-2-(4-fluorophenyl)cyclopentan-1-yl)-3-hydroxypyrrolidin-2-one (0.20 gm, 0.39 mmol) prepared as in Example 8 in acetone (3 mL) was added 8N Jones reagent (0.150 mL). After 30 min, the mixture was diluted with water and extracted twice with ethyl acetate. The ethyl acetate layers were each successively washed with brine containing some sodium bicarbonate solution, combined, and dried over sodium sulfate. Removal of solvent in vacuo and purification by FC (2% methanol/methylene chloride) afforded the title intermediate. HPLC/MS: m/e=518 (M+1).

Step B: (3R,5R and 3S,5R)-5-(((1R),(2R),(3S))-3-((1R)-1-(3,5-bis(Trifluoromethyl)phenyl)-ethoxy)-2-(4-fluorophenyl)cyclopentan-1-yl)-3-hydroxy-3-methylpyrrolidin-2-one To a solution of (5R)-5-(((1R),(2R),(3S))-3-((1R)-1-(3,5-bis(trifluoromethyl)phenyl)-ethoxy)-2-(4-fluorophenyl)cyclopentan-1-yl)-3-oxoypyrrolidin-2-one (62 mg, 0.12 mmol) from Step A in THF (2 mL) was added at rt 1.4 M methyl magnesium bromide (0.146 mL). After 1 hr, the reaction was quenched into with water and 2N HCl and extracted twice with ethyl acetate. The ethyl acetate layers were each successively washed with brine containing some sodium bicarbonate solution, combined, and dried over sodium sulfate. Removal of solvent in vacuo and purification by Prep TLC (2% methanol/methylene chloride) afforded the title products as a mixture of isomers. These were separated on a Chiracel OD column (6% isopropanol-heptanes). Faster isomer; HPLC/MS: m/e=534 (M+1g), Rt=3.73 min. NMR (CDCl$_3$): □ 1.32 (s, 3 H), 1.41 (d, J=6.5 Hz, 3 H), 1.6–1.79 (m, 2 H), 1.80–1.91 (m, 1 H), 1.91–2.01 (m, 1 H), 2.01–2.16 (m, 3 H), 2.41 (br s, 1 H), 2.74 (dd, J=7.4 and 10.3 Hz, 1 H), 3.69 (q, J =6.2 Hz, 1 H), 3.74 (q, J=6.9 Hz, 1 H), 4.52 (q, J=6.6 Hz, 1 H), 6.03 (br s, 1 H), 6.98 (br t, J=8.7 Hz, 2 H), 7.02–7.07 (m, 2 H), 7.46 (s, 2 H), 7.72 (s, 1 H). Slower isomer; HPLC/MS: m/e=534 (M+1), Rt=3.71 min. NMR (CDCl$_3$): □ 1.36 (s, 3 H), 1.42 (d, J=6.6 Hz, 3 H), 1.67 (dd, 1 H), 1.74–1.91 (m, 3 H), 1.94–2.04 (m, 2 H), 2.06–2.18 (m, 2 H), 2.79 (dd, J=7.1 and 9.8 Hz, 1 H), 3.50 (dt, J=8.0 and 8.5 Hz, 1 H), 3.68 (q, J=5.7 Hz, 1 H), 4.53 (q, J=6.4 Hz, 1 H), 6.33 (br s, 1 H), 6.97 (br t, J=8.7 Hz, 2 H), 7.03–7.08 (m, 2 H), 7.47 (s, 2 H), 7.73 (s, 1 H).

EXAMPLE 13

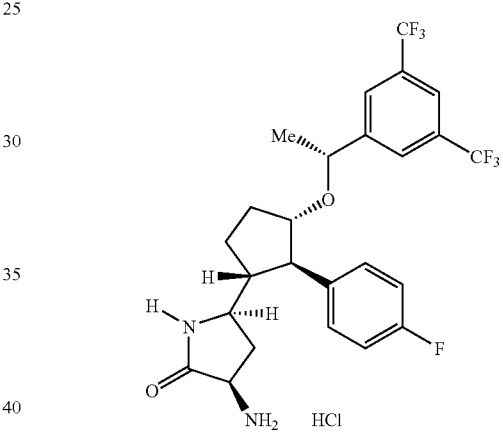

(3R,5R)-5-(((1R),(2R),(3S))-3-((1R)-1-(3,5-bis(Trifluoromethyl)phenyl)ethoxy)-2-(4-fluorophenyl)cyclopentan-1-yl)-3-aminopyrrolidin-2-one hydrochloride salt Step A: (3R,5R and 3S,5R)-5-(((1R),(2R),(3S))-3-((1R)-1-(3,5-bis(Trifluoromethyl)-phenyl)ethoxy)-2-(4-fluorophenyl)cyclopentan-1-yl)-3-mesylpyrrolidin-2-one To a solution of (3R,5R and 3S,5R)-5-(((1R),(2R),(3S))-3-((1R)-1-(3,5-bis(trifluoromethyl)phenyl)ethoxy)-2-(4-fluorophenyl)cyclopentan-1-yl)-3-hydroxypyrrolidin-2-one (0.295 gm, 0.57 mmol) prepared as in Example 8 (prior to separation of the hydroxy isomers) in methylene chloride (3 mL) cooled in an ice bath were added TEA (0.094 mL) and mesyl chloride (0.044 mL). After 10 min, the mixture was allowed to warm to rt for 30 min at which time additional TEA (0.040 mL) and mesyl chloride (0.020 mL) were added. The reaction was stirred at rt for 20 min before being quenched into dilute aq. HCl. The mixture was diluted with water and extracted twice with ethyl acetate. The ethyl acetate layers were each successively washed with brine containing some sodium bicarbonate solution, combined, and dried over sodium sulfate. Removal of solvent in vacuo and purification by FC (25–50% ethyl acetate/hexanes) afforded the title intermediates as the major, higher Rf (3S,5R) isomer and minor, lower Rf (3R,5R) isomer.

Step B: (3R,5R)-5-(((1R),(2R),(3S))-3-((1R)-1-(3,5-bis(Trifluoromethyl)phenyl)ethoxy)-2-(4-fluorophenyl)cyclopentan-1-yl)-3-azidopyrrolidin-2-one To a solution of (3S,5R)-5-(((1R),(2R),(3S))-3-((1R)-1-(3,5-bis(trifluoromethyl)phenyl)-ethoxy)-2-(4-fluorophenyl)cyclopentan-1-yl)-3-mesylpyrrolidin-2-one (170 mg, 0.284 mmol) from Step A (higher Rf) in DMF (2 mL) was added sodium azide (185 mg). The reaction was heated at 80° C. for 16 hr. The mixture was diluted with water and extracted twice with ether. The ether layers were each successively washed with brine containing some sodium bicarbonate solution, combined, and dried over sodium sulfate. Removal of solvent in vacuo and purification by FC (25–50% ethyl acetate/hexanes) afforded the title intermediate. HPLC/MS: m/e=545 (M+1), Rt=4.13 min. NMR (CDCl$_3$): □ 1.3–1.4 (m, 1 H), 1.42 (d, J=6.4 Hz, 3 H), 1.71–1.81 (m, 1 H), 1.81–1.91 (m, 1 H), 1.94–2.03 (m, 1 H), 2.06–2.16 (m, 2 H), 2.23–2.30 (m, 1 H), 2.75 (dd, J=7.1 and 9.8 Hz, 1 H), 3.57 (q, J=8.0 Hz, 1 H), 3.68 (q, J=6.0 Hz, 1 H), 4.07 (t, J=9 Hz, 1 H), 4.52 (q, J=6.4 Hz, 1 H), 6.49 (br s, 1 H), 6.98 (br t, J=8.7 Hz, 2 H), 7.03–7.08 (m, 2 H), 7.46 (s, 2 H), 7.72 (s, 1 H).

Step C: (3R,5R)-5-(((1R),(2R),(3S))-3-((1R)-1-(3,5-bis(Trifluoromethyl)phenyl)ethoxy)-2-(4-fluorophenyl)cyclopentan-1-yl)-3-aminoopyrrolidin-2-one hydrochloride salt A solution of (3R,5R)-5-(((1R),(2R),(3S))-3-((1R)-1-(3,5-bis(trifluoromethyl)phenyl)ethoxy)-2-(4-fluorophenyl)cyclopentan-1-yl)-3-azidopyrrolidin-2-one (112 mg) from Step B was hydrogenated over 20% Pd(OH)$_2$/C (40 mg) as in Example 3, Step E, in the presence of 2N HCl in ether (0.20 mL) to afford the title product HCl salt after filtration and evaporation of solvent. HPLC/MS: m/e=519 (M+1), Rt=3.21 min.

EXAMPLE 14

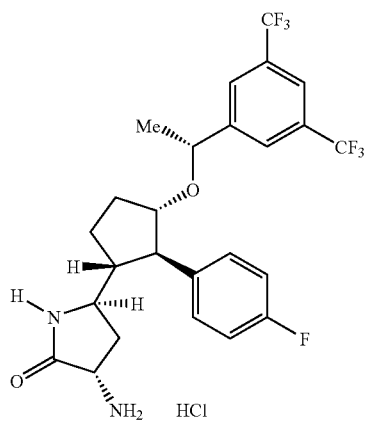

(3S,5R)-5-(((1R),(2R),(3S))-3-((1R)-1-(3,5-bis(Trifluoromethyl)phenyl)ethoxy)-2-(4-fluorophenyl)cyclopentan-1-yl)-3-aminopyrrolidin-2-one hydrochloride salt Using essentially the same procedures as in Example 13, Steps B–C, but starting with the minor, lower mesylate (3R,5R)-5-(((1R),(2R),(3S))-3-((1R)-1-(3,5-bis(trifluoromethyl)phenyl)ethoxy)-2-(4-fluorophenyl)cyclopentan-1-yl)-3-mesylpyrrolidin-2-one from Step A, the title product was obtained. HPLC/MS: m/e=519 (M+1), Rt=3.21 min. Azide intermediate NMR (CDCl$_3$): □ 1.40 (d, J=6.4 Hz, 3 H), 1.68–1.78 (m, 1 H), 1.78–1.91 (m, 3 H), 1.91–1.98 (m, 1 H), 1.98–2.06 (m, 1 H), 2.10–2.18 (m, 1 H), 2.75 (dd, J=7.5 and 10.5 Hz, 1 H), 3.65 (br q, 1 H), 3.72 (q, J=6.0 Hz, 1 H), 4.04 (dd, J=5.9 and 8.2 Hz, 1 H), 4.51 (q, J=6.4 Hz, 1 H), 6.97 (br t, J=8.7 Hz, 2 H), 7.07–7.13 (m, 2 H), 7.45 (s, 2 H), 7.67 (br s, 1 H), 7.71 (s, 1 H).

EXAMPLE 15

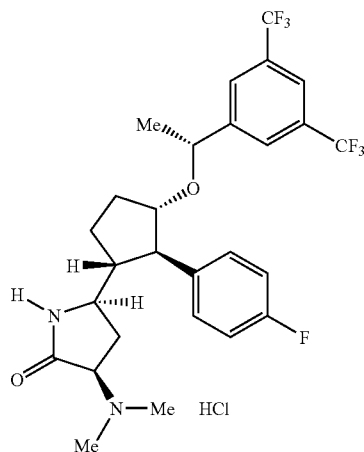

(3R,5R)-5-(((1R),(2R),(3S))-3-((1R)-1-(3,5-bis(Trifluoromethyl)phenyl)ethoxy)-2-(4-fluorophenyl)cyclopentan-1-yl)-3-dimethylaminopyrrolidin-2-one hydrochloride salt To a solution of (3R,5R)-5-(((1R),(2R),(3S))-3-((1R)-1-(3,5-bis(trifluoromethyl)phenyl)-ethoxy)-2-(4-fluorophenyl)cyclopentan-1-yl)-3-aminopyrrolidin-2-one (20 mg, 0.036 mmol) from Example 13 in 1,2-dichloroethane (1 mL) was added 37% by wt aq formaldehyde (0.015 mL), DIPEA (0.0063 mL), and sodium triacetoxy borohydride (23 mg) and the reaction was stirred at rt for 16 hr. The mixture was diluted with water and extracted twice with methylene chloride. The organic layers were each successively washed with brine containing some sodium carbonate solution, combined, and dried over sodium sulfate. Removal of solvent in vacuo and purification by Prep TLC (5% methanol/methylene chloride) afforded the title compound after formation of the hydrochloride salt with 2N HCl in ether and evaporation. HPLC/MS: m/e=547 (M+1), Rt=3.23 min. NMR (CDCl$_3$): □ 1.39 (d, J=6.6 Hz, 3 H), 1.38–1.47 (m, 1 H), 1.74–1.88 (m, 2 H), 1.93–2.05 (m, 3 H), 2.05–2.16 (m, 1 H), 2.10–2.18 (m, 1 H), 2.35 (s, 6 H), 2.78 (dd, J=7.5 and 10 Hz, 1 H), 3.4–3.5 (m, 2 H), 3.69 (m, 1 H), 4.51 (q, J=6.6 Hz, 1 H), 6.96 (br t, J=8.7 Hz, 2 H), 7.04–7.08 (m, 2 H), 7.33 (br s, 1 H), 7.44 (s, 2 H), 7.71 (s, 1 H).

EXAMPLE 16

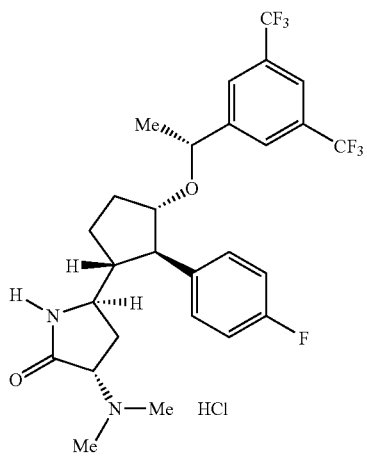

(3S,5R)-5-(((1R),(2R),(3S))-3-((1R)-1-(3,5-bis(Trifluoromethyl)phenyl)ethoxy)-2-(4-fluorophenyl)cyclopentan-1-yl)-3-dimethylaminopyrrolidin-2-one hydrochloride salt Using essentially the same procedures as in Example 15, but starting with (3S,5R)-5-(((1R),(2R),(3S))-3-((1R)-1-(3,5-bis(trifluoromethyl)phenyl)ethoxy)-2-(4-fluorophenyl)cyclopentan-1-yl)-3-dimethylaminopyrrolidin-2-one from Example 14, the title product was obtained. HPLC/MS: m/e=519 (M+1), Rt=3.21 min.

EXAMPLE 17

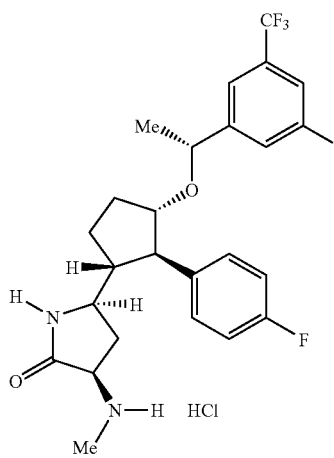

(3R,5R)-5-(((1R),(2R),(3S))-3-((1R)-1-(3,5-bis(Trifluoromethyl)phenyl)ethoxy)-2-(4-fluorophenyl)cyclopentan-1-yl)-3-methylaminopyrrolidin-2-one hydrochloride salt A solution of (3R,5R)-5-(((1R),(2R),(3S))-3-((1R)-1-(3,5-bis(trifluoromethyl)phenyl)-ethoxy)-2-(4-fluorophenyl)cyclopentan-1-yl)-3-aminopyrrolidin-2-one (25 mg, 0.048 mmol) prepared as in Example 13, 1-hydroxymethylbenztriazole (7.2 mg), and DIPEA (0.017 mL) were stirred in methanol (2 mL) for 16 hrs and was then evaporated. The residue was taken up in methanol (2 mL) and hydrogenated for 2 hr at 45 psi over 20% Pd(OH)$_2$/C (40 mg) as in Example 3, Step E. HPLC/MS indicated a mixture of statring material, mono- and di-methylation. The title compound was isolated by RP prep HPLC and converted to the hydrochloride salt with 2N HCl in ether. HPLC/MS: m/e=533 (M+1), Rt=3.25 min.

EXAMPLE 18

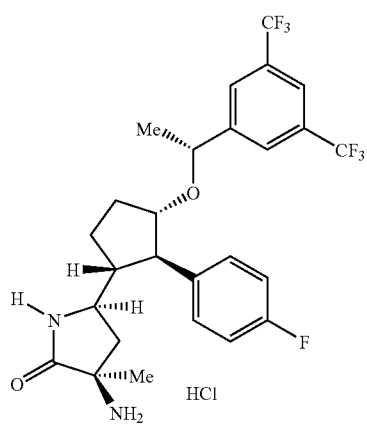

(3R,5R)-5-(((1R),(2R),(3S))-3-((1R)-1-(3,5-bis(Trifluoromethyl)phenyl)ethoxy)-2-(4-fluorophenyl)cyclopent-1-yl)-3-amino-3-methylpyrrolidin-2-one hydrochloride salt

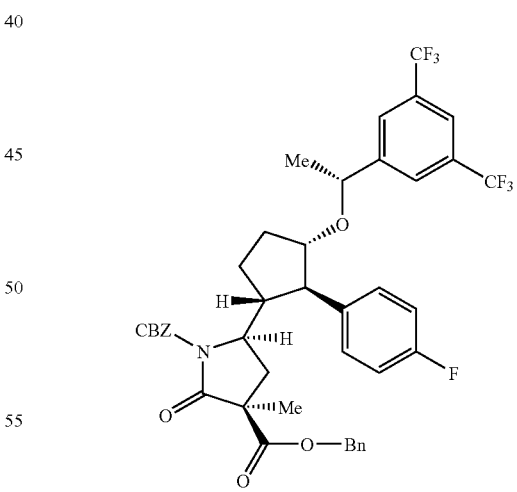

Step A: (3R,5R)-5-(((1R),(2R),(3S))-3-((1R)-1-(3,5-bis(Trifluoromethyl)phenyl)ethoxy)-2-(4-fluorophenyl)cyclopent-1-yl)-1,3-dibenzyloxycarbonyl-3-methylpyrrolidin-2-one A solution of (5R)-5-(((1R),(2R),(3S))-3-((1R)-1-(3,5-bis(trifluoromethyl)phenyl)-ethoxy)-2-(4-fluorophenyl)cyclopentan-1-yl)-1-benzyloxycarbonylpyrrolidin-2-one (13 gm, 20.4 mmol) (prepared as in Example 3, Step D, (dried by prior evaporation of 100 mL of toluene) in THF (200 mL) under nitrogen was cooled to −25° C. in an ice/dry ice/methanol bath and benzyl chloroformate (3.2 mL) was added. After stirring for 10 min, 1 M NaHMDS (51 mL) was added slowly over 10 min. The reaction was allowed to warm to −15° C. over 30 min at which time TLC (30% ethyl acetate/hexanes) of an aliquot (quenched into ethyl acetate/2N HCl) indicated that the starting material was essentially gone. Methyl iodide (12.7 mL) was added and the reaction was allowed to warm to rt for 1 hr and was then warmed in a water bath to 30° C. for 2–3 hr. The reaction was monitored by HPLC/MS for the intermediate (m/e=728 (M+1−44, 100%), Rt=4.64 min) and product (m/e=742 (M+1−44, 100%), Rt=4.69 min) and was about 90% complete. The reaction was then stored at 0° C. overnight at which time the methylation was deemed essentially complete and the reaction was slowly quenched into a stirred mixture of ethyl acetate, water, and excess 2N HCl solution. The mixture was extracted twice with ethyl acetate and the ethyl acetate layers were each successively washed with brine containing some sodium bicarbonate solution, combined, and dried over sodium sulfate. Removal of solvent in vacuo and purification by FC (10–50% ethyl acetate/hexanes) afforded the title intermediate. The (5S) isomer (5–10%) is slightly higher Rf and was normally only partially separated at this step since it can be removed in subsequent steps. However on smaller scale, the minor, higher Rf isomer can be isolated. HPLC/MS: m/e=742 (M+1−44, 100%), 786 (M+1); Rt=4.69 min NMR (CDCl₃) (Major, lower (3R,5R) isomer): □ 1.37 (d, J=6.6 Hz, 3 H), 1.48 (s, 3 H), 1.58–1.66 (m, 1 H), 1.71–1.85 (m, 2 H), 1.95–2.05 (m, 2 H), 2.50 (dd, J=6.6 and 12 Hz, 1 H), 2.84–2.92 (m, 1 H), 2.86 (dd, J=6.6 and 10 Hz, 1 H), 3.59 (q, J=6.4 Hz, 1 H), 4.33 (br q, J=7 Hz, 1 H), 4.48 (q, J=6.6 Hz, 1 H), 4.76 and 4.98 (ABq, J=12.5 Hz, 2 H), 5.22 and 5.25 (ABq, J=11 Hz, 2 H), 6.73–6.83 (m, 4 H), 7.3–7.46 (m, 5 H), 7.42 (s, 2 H), 7.69 (s, 1 H).

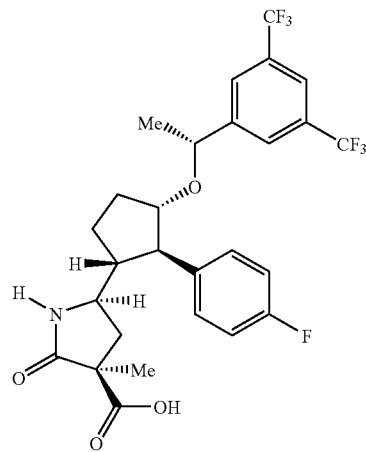

Step B: (3R,5R)-5-(((1R),(2R),(3S))-3-((1R)-1-(3,5-bis(Trifluoromethyl)phenyl)ethoxy)-2-(4-fluorophenyl)cyclopent-1-yl)-3-carboxy-3-methylpyrrolidin-2-one A solution of (3R,5R)-5-(((1R),(2R),(3S))-3-((1R)-1-(3,5-bis(trifluoromethyl)phenyl)-ethoxy)-2-(4-fluorophenyl)cyclopent-1-yl)-1,3-dibenzyloxycarbonyl-3-methylpyrrolidin-2-one (22.5 gm, 28.7 mmol) (prepared as in Step A) in methanol (500 mL) was hydrogenated over 20% Pd(OH)₂/C (2.0 gm) on a Parr shaker at 45 p.s.i. in a 2 L flask. After 6 hr, HPLC/MS indicated mostly product acid (m/e=562 (M+1), Rt=3.89 min) and a trace of methyl ester (m/e=576 (M+1), Rt=4.13 min), but still some intermediate benzyl ester (m/e=652 (M+1), Rt=4.38 min). Thus, an additional portion of 20% Pd(OH)₂/C (0.5 gm) was added and the hydrogenation was continued for another 16 hr, at which time HLPC/MS indicated that the hydrogenation was essentially complete. The reaction was filtered to remove catalyst and was evaporated to dryness to afford the title acid. This material was routinely used without purification after evaporating a portion of toluene to remove residual water and methanol. A portion was recrystallized from ethyl acetate/heptanes and then again from nitromethane to afford x-ray quality crystals which confirmed the indicated stereochemistries. HPLC/MS: m/e=562 (M+1); Rt=3.89 min NMR (CDCl₃) (Major (3R,5R) isomer): □ 1.39 (d, J=6.6 Hz, 3 H), 1.47 (s, 3 H), 1.64–1.76 (m, 1 H), 1.76–1.87 (m, 1 H), 1.87–2.01 (m, 2 H), 2.01–2.11 (m, 2 H), 2.11–2.18 (m, 1 H), 2.75 (dd, J=6.5 and 9.4 Hz, 1 H), 3.63 (t, J=5.4 Hz, 1 H), 3.69 (m, 1 H), 4.50 (q, J=6.6 Hz, 1 H), 6.67 (br s, 1 H), 6.93 (m, 2 H), 6.98 (m, 2 H), 7.44 (s, 2 H), 7.69 (s, 1 H).

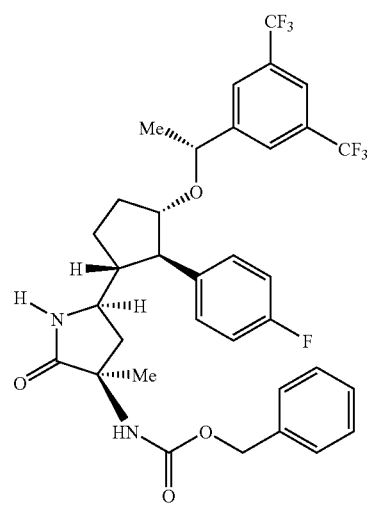

Step C: (3R,5R)-5-(((1R),(2R),(3S))-3-((1R)-1-(3,5-bis(Trifluoromethyl)phenyl)ethoxy)-2-(4-fluorophenyl)cyclopent-1-yl)-3-benzyloxycarbonylamino-3-methylpyrrolidin-2-one To a solution of (3R,5R)-5-(((1R),(2R),(3S))-3-((1R)-1-(3,5-bis(trifluoromethyl)phenyl)-ethoxy)-2-(4-fluorophenyl)cyclopent-1-yl)-3-carboxy-3-methylpyrrolidin-2-one (15 gm, 26.7 mmol) (prepared as in Step B and dried by evaporation of 100 mL of toluene) in acetone (200 mL) was added at rt DIPEA (12 mL) and then isobutyl chloroformate (5.25 mL). The reaction was-stirred at rt for 40 min and was then cooled to 0° C. in an ice/brine bath. This solution was slowly added to a cold solution of sodium azide (8.7 gm) in water (150 mL) and acetone (150 mL) maintaining the temperature at <10° C. The mixture was stirred for 45 min (HPLC/MS indicated some acid, but mostly acyl azide, m/e=587 (M+1), Rt=4.22) and then most of the acetone was removed in vacuo without heating. The mixture was diluted with ice water and was extracted twice with toluene. The toluene layers were each successively washed with cold brine containing some sodium bicarbonate solution, combined, and dried over sodium sulfate. About ⅔ of the solvent was removed in vacuo without heating to afford a dry toluene solution of the acyl azide intermediate. (Note: It is very important to keep the solution cold to prevent rearrangement to the isocyanate prior to complete drying by azeotroping any water and acetone during removal of the toluene. Also, the residual isobutanol must be removed at this time. However, the acyl azide should not be concentrated to dryness due to the exothermic loss of nitrogen during the subsequent rearrangement.) The above toluene solution of acyl azide (~200 mL) was heated to 85° C. under nitrogen for 1–2 hr (nitrogen bubbling ceases and HPLC/MS indicated acyl azide was gone, isocyanate m/e=559 (M+1), Rt=4.29 min) and was then further concentrated to 100 mL. To this solution was added benzyl alcohol (28 mL), DIPEA (14 mL), and DMAP (200 mg, cat) and the mixture was reheated to 85° C. for 3–4 hr (monitored by HPLC/MS for loss of isocyanate, m/e=559 (M+1), Rt=4.29 min; product, m/e=667 (M+1), Rt=4.23 min). The mixture was concentrated in vacuo and purified by FC (20–80% ethyl acetate/hexanes) to remove some of the residual (3S,5S) and (3R,5S) isomers and afforded the title intermediate (>95% (3R,5R) isomer). Any residual amounts of (3S,5S) and (3R,5S) isomers were removed by preparative reverse phase HPLC (0.1% TFA in 70% acetonitrile/water). The product fractions were combined, sodium bicarbonate added to neutralize TFA, acetonitrile was mostly removed in vacuo, the product was extracted from the aqueous with 2× ethyl acetate, and the solvent was evaporated after drying with sodium sulfate to afford the title CBZ intermediate (10 gm) and 2.8 gm mixed fractions after the main isomer peak. The mixed fractions could be further purified by Chiracel OD to obtain additional product (Rt=8 min), as well as the minor (3S,5R) isomer (Rt=22.5 min) and variable amounts of the (3S,5S) isomer (Rt=10.5 min). NMR (CDCl₃) (Major, (3R,5R) isomer): □ 1.37 (s, 3 H), 1.40 (d, J=6.4 Hz, 3 H), 1.78–1.9 (m, 2 H), 1.91–2.0 (m, 1 H), 2.0–2.25 (m, 3 H), 2.79 (dd, J=6.6 and 12 Hz, 1 H), 3.52–3.61 (m, 1 H), 3.65 (q, J=6.4 Hz, 1 H), 4.52 (q, J=6.6 Hz, 1 H), 5.05 and 5.09 (ABq, 2 H), 5.29 (br s, 1 H), 6.23 (br s, 1 H), 6.96 (br t, 2 H), 7.04 (br m, 2 H), 7.32–7.41 (m, 5 h), 7.47 (s, 2 H), 7.72 (s, 1 H). NMR (CDCl₃) (Minor, (3S,5R) isomer): □ 1.26 (s, 3 H), 1.36 (d, J=6.5 Hz, 3 H), 1.50 (dd, 1 H), 1.6–1.73 (m, 1 H), 1.73–1.85 (m, 1 H), 1.85–2.3 (m, 4 H), 2.47 (dd, J=6.6 and 12 Hz, 1 H), 2.67 (dd, J=6.6 and 12 Hz, 1 H), 3.61 (q, J=6.3 Hz, 1 H), 3.80 (br s, 1 H), 4.46 (q, J=6.4 Hz, 1 H), 4.99 and 5.05 (ABq, J=12.2 Hz, 1 H), 6.12 (br s, 1 H), 6.92 (br t, 2 H), 6.98 (br m, 2 H), 7.26–7.38 (m, 5 H), 7.40 (s, 2 H), 7.66 (s, 1 H). NMR (CDCl₃) (lactam (3S,5S) isomer): □ 1.34 (s, 3 H), 1.36 (d, J=6.5 Hz, 3 H), 1.55–1.71 (m, 1 H), 1.71–1.84 (m, 1 H), 1.84–1.95 (m, 1 H), 1.95–2.2 (m, 3 H), 2.47 (dd, J=6.6 and 12 Hz, 1 H), 2.73 (t, 1 H), 3.45 (q, J=6.3 Hz, 1 H), 3.64 (m, 1 H), 4.44 (q, J=6.4 Hz, 1 H), 4.97 (br s, 1 H), 5.03 and 5.08 (ABq, 1 H), 5.32 (br s, 1 H), 6.95 (br t, 2 H), 7.05 (br m, 2 H), 7.28–7.38 (m, 5 H), 7.36 (s, 2 H), 7.66 (s, 1 H).

Step D: (3R,5S)-5-(((1R),(2R),(3S))-3-((1R)-1-(3,5-bis(Trifluoromethyl)phenyl)ethoxy)-2-(4-fluorophenyl)cyclopent-1-yl)-3-amino-3-methylpyrrolidin-2-one hydrochloride salt A solution of (3R,5R)-5-(((1R),(2R),(3S))-3-((1R)-1-(3,5-bis(trifluoromethyl)-phenyl)ethoxy)-2-(4-fluorophenyl)cyclopent-1-yl)-3-benzyloxycarbonylamino-3-methylpyrrolidin-2-one (12.5 gm, 18.7 mmol) (prepared as in Step C) in methanol (100 mL) and 2N HCl in ether (19 mL) was hydrogenated over 20% Pd(OH)₂/C (0.65 gm) on a Parr shaker at 45 p.s.i. for 90 min. HPLC/MS indicated product (m/e=533 (M+1), Rt=3.33 min) and only a trace of N-methylation (m/e=547 (M+1), Rt=3.35 min). The reaction was filtered to remove catalyst and was evaporated to dryness to afford the title compound as the hydrochloride salt. This material was triturated three times with ether (200 mL each) to afford the final product as a white solid (10.2 gm) after vacuum drying. HPLC/MS: m/e=532 (M+1); Rt=3.25 min NMR (CD₃OD) (Major (3R,5R) isomer): □ 1.31 (d, J=6.5 Hz, 3 H), 1.35 (s, 3 H), 1.46 (dd, J=9.3 and 12.6 Hz, 1 H), 1.67–1.84 (m, 2 H), 1.93–2.08 (m, 3 H), 2.14–2.23 (m, 1 H), 2.79 (dd, J=6.6 and 12 Hz, 1 H), 3.59 (dt, 1 H), 3.72 (q, J=7.6 Hz, 1 H), 4.62 (q, J=6.6 Hz, 1 H), 6.91 (m, 2 H), 7.13 (m, 2 H), 7.50 (s, 2 H), 7.70 (s, 1 H). Use of nOe experiments confirmed the relative lactam stereochemistry as (3R,5R).

EXAMPLE 19

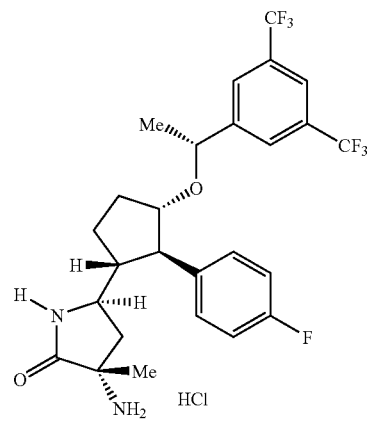

(3S,5R)-5-(((1R),(2R),(3S))-3-((1R)-1-(3,5-bis(Trifluoromethyl)phenyl)ethoxy)-2-(4-fluorophenyl)cyclopent-1-yl)-3-amino-3-methylpyrrolidin-2-one hydrochloride salt Using essentially the same procedures as in Example 18, but using the higher Rf (3S,5R)-5-(((1R),(2R),(3S))-3-((1R)-1-(3,5-bis(trifluoromethyl)phenyl)ethoxy)-2-(4-fluorophenyl)cyclopent-1-yl)-1,3-dibenzyloxycarbonyl-3-methylpyrrolidin-2-one from Step A or the slower (3S,5R)-5-(((1R),(2R),(3S))-3-((1R)-1-(3,5-bis(trifluoromethyl)phenyl)ethoxy)-2-(4-fluorophenyl)cyclopent-1-yl)-3-benzyloxycarbonylamino-3-methylpyrrolidin-2-one (Rt=22.5 min) from Step C, the title product was obtained. HPLC/MS: m/e=532 (M+1); Rt=3.26 min

EXAMPLE 20

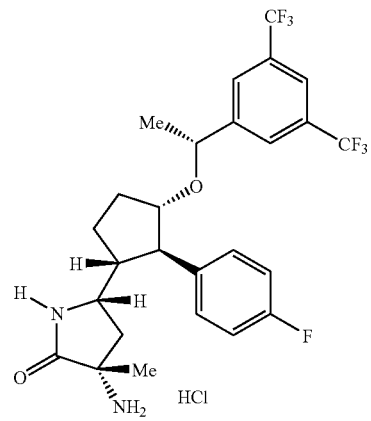

(3S,5S)-5-(((1R),(2R),(3S))-3-((1R)-1-(3,5-bis(Trifluoromethyl)phenyl)-2-(4-fluorophenyl)cyclopent-1-yl)-3-amino-3-methylpyrrolidin-2-one hydrochloride salt Using essentially the same procedures as in Example 18, but starting with (5S)-5-(((1R),(2R),(3S))-3-((1R)-1-(3,5-bis(trifluoromethyl)phenyl)ethoxy)-2-(4-fluorophenyl)cyclopentan-1-yl)-1-benzyloxycarbonylpyrrolidin-2-one from Example 4 or using the middle (3S,5S)-5-(((1R),(2R),(3S))-3-((1R)-1-(3,5-bis(trifluoromethyl)phenyl)ethoxy)-2-(4-fluorophenyl)cyclopent-1-yl)-3-benzyloxycarbonylamino-3-methylpyrrolidin-2-one (Rt=10.5 min) from Example 18, Step C, the title product was obtained. HPLC/MS: m/e=532 (M+1); Rt=3.26 min

EXAMPLE 21

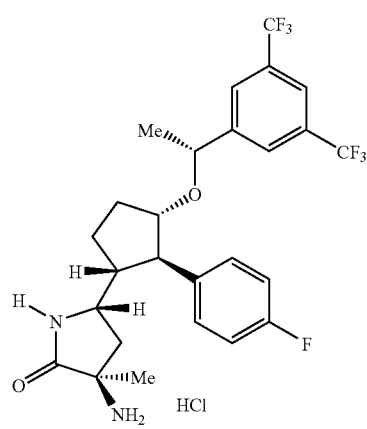

(3R,5S)-5-(((1R),(2R),(3S))-3-((1R)-1-(3,5-bis(Trifluoromethyl)phenyl)ethoxy)-2-(4-fluorophenyl)cyclopent-1-yl)-3-amino-3-methylpyrrolidin-2-one hydrochloride salt Using essentially the same procedures as in Example 18, but starting with (5S)-5-(((1R),(2R),(3S))-3-((1R)-1-(3,5-bis(trifluoromethyl)phenyl)ethoxy)-2-(4-fluorophenyl)cyclopentan-1-yl)-1-benzyloxycarbonylpyrrolidin-2-one from Example 4 and using the faster (3R,5S)-5-(((1R),(2R),(3S))-3-((1R)-1-(3,5-bis(trifluoromethyl)phenyl)ethoxy)-2-(4-fluorophenyl)cyclopent-1-yl)-3-benzyloxycarbonylamino-3-methylpyrrolidin-2-one (Rt=8.2 min) as in Example 18, Step C, the title product was obtained. HPLC/MS: m/e=532 (M+1); Rt=3.26 min

EXAMPLE 22

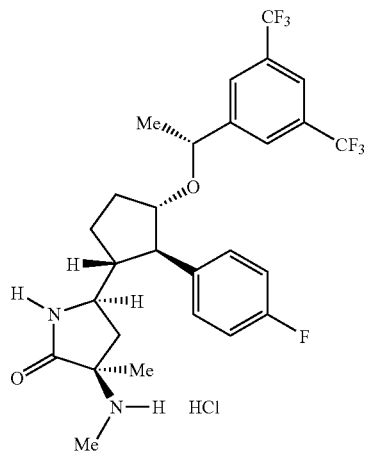

(3R,5R)-5-(((1R),(2R),(3S))-3-((1R)-1-(3,5-bis(Trifluoromethyl)phenyl)ethoxy)-2-(4-fluorophenyl)-cyclopent-1-yl)-3-aminomethyl-3-methylpyrrolidin-2-one hydrochloride salt Using essentially the same procedures as in Example 17, but starting with (3R,5R)-5-(((1R),(2R),(3S))-3-((1R)-1-(3,5-bis(trifluoromethyl)phenyl)ethoxy)-2-(4-fluorophenyl)cyclopent-1-yl)-3-amino-3-methylpyrrolidin-2-one hydrochloride salt (30 mg) from Example 18, the title compound was obtained. HPLC/MS: m/e=547 (M+1); Rt=3.28 min

EXAMPLE 23

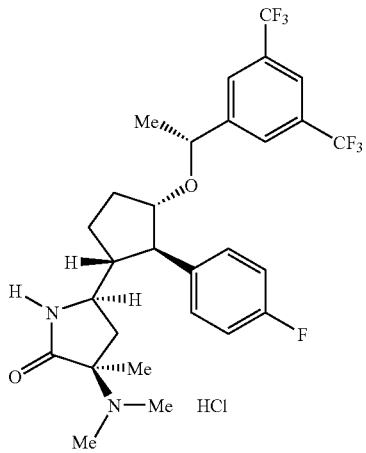

(3R,5R)-5-(((1R),(2R),(3S))-3-((1R)-1-(3,5-bis(Trifluoromethyl)phenyl)ethoxy)-2-(4-fluorophenyl)cyclopent-1-yl)-3-dimethylamino-3-methylpyrrolidin-2-one hydrochloride salt Using essentially the same procedures as in Example 16, but starting with (3R,5R)-5-(((1R),(2R),(3S))-3-((1R)-1-(3,5-bis(trifluoromethyl)phenyl)ethoxy)-2-(4-fluorophenyl)cyclopent-1-yl)-3-amino-3-methylpyrrolidin-2-one hydrochloride salt (30 mg) from Example 18, the title compound was obtained. HPLC/MS: m/e=561 (M+1); Rt=3.31 min While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

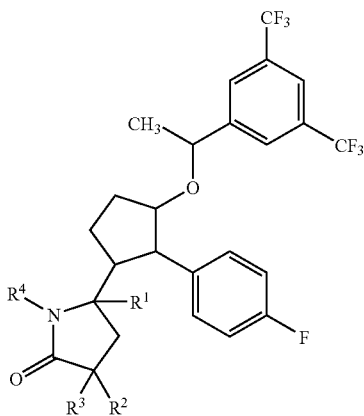

I wherein:
R$^1$ is selected from the group consisting of:
(1) hydrogen, and
(2) C$_{1-6}$alkyl;
R$^2$ is selected from the group consisting of:
(1) hydrogen,
(2) —OH,
(3) —NH$_2$,
(4) —NH(C$_{1-6}$alkyl), and
(5) —N(C$_{1-6}$alkyl)(C$_{1-6}$alkyl);
R$^3$ is selected from the group consisting of:
(1) hydrogen, and
(2) C$_{1-6}$alkyl;
R$^4$ is selected from the group consisting of:
(1) hydrogen, and
(2) C$_{1-6}$alkyl;
and pharmaceutically acceptable salts thereof and individual enantiomers and diastereomers thereof.

2. The compound of claim 1 of the formula Ia:

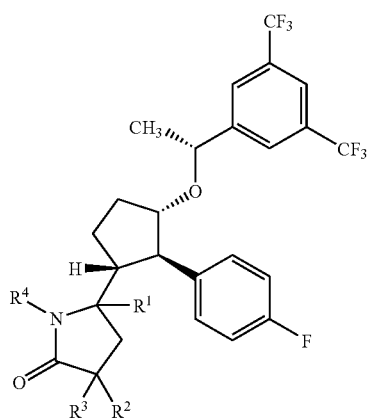

Ia and pharmaceutically acceptable salts thereof and individual enantiomers and diastereomers thereof.

3. The compound of claim 1 wherein R$^1$ is selected from the group consisting of:
(1) hydrogen, and
(2) methyl.

4. The compound of claim 1 wherein R$^2$ is selected from the group consisting of:
(1) hydrogen,
(2) —OH, and
(3) —NH$_2$.

5. The compound of claim 1 wherein R$^3$ is selected from the group consisting of:
(1) hydrogen, and
(2) methyl.

6. The compound of claim 1 wherein:
R$^1$ is hydrogen;
R$^2$ is selected from the group consisting of:
(1) hydrogen,
(2) —OH, and
(3) —NH$_2$;
R$^3$ is selected from the group consisting of:
(1) hydrogen, and
(2) methyl; and
R$^4$ is hydrogen.

7. A compound which is selected from the group consisting of:

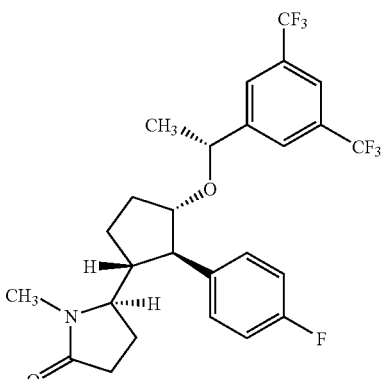

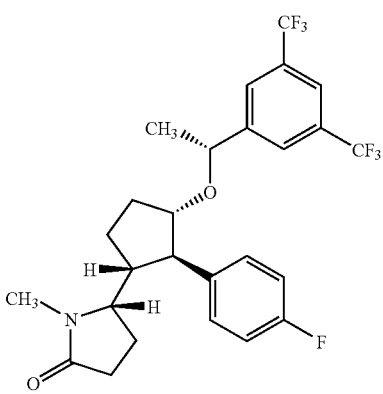

-continued
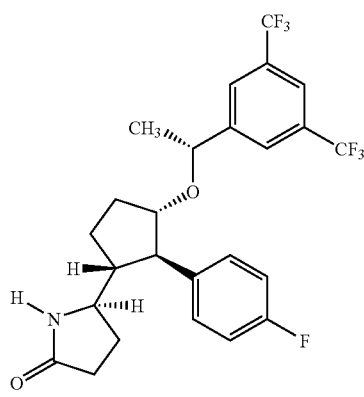
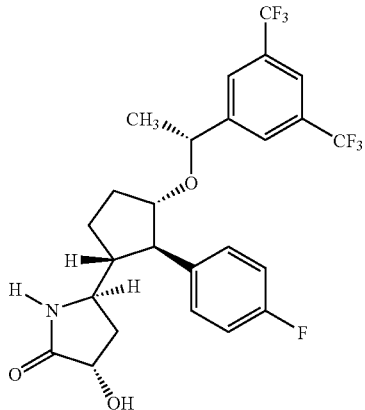

-continued
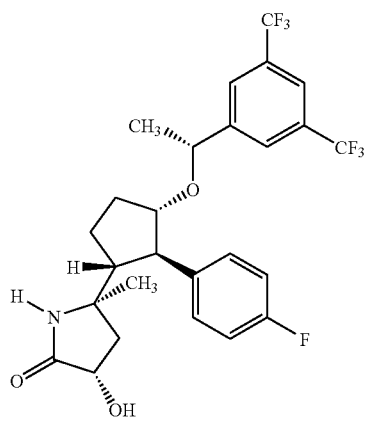
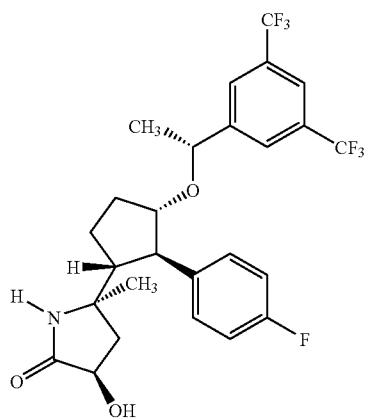
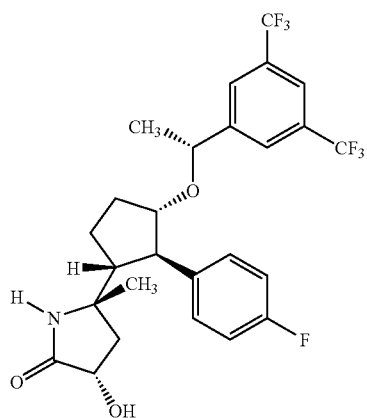
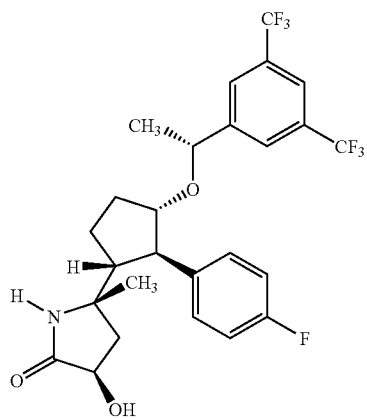
-continued
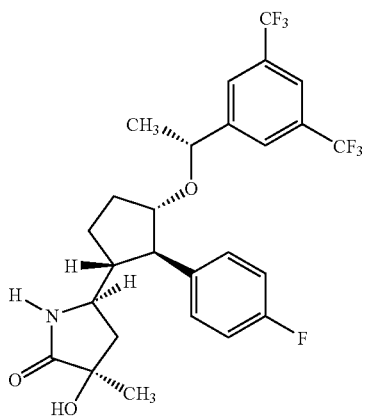
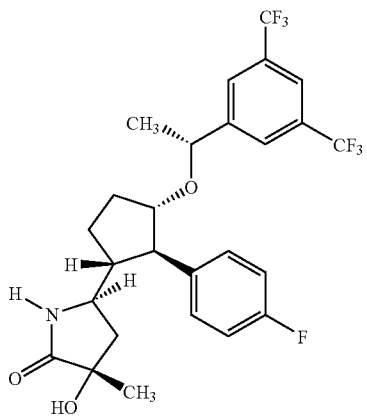
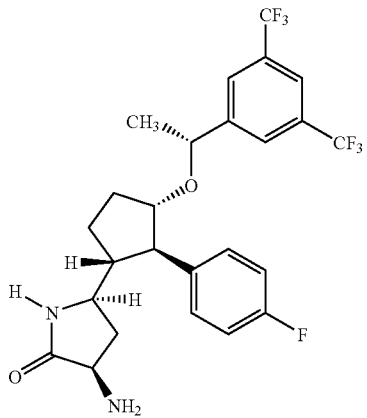
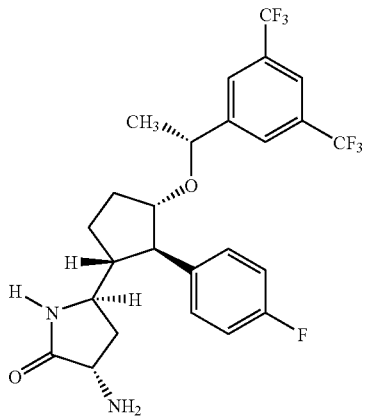

-continued
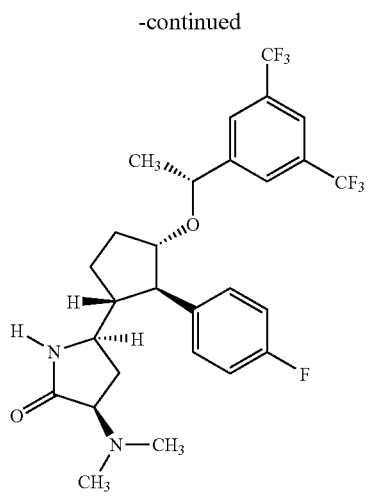
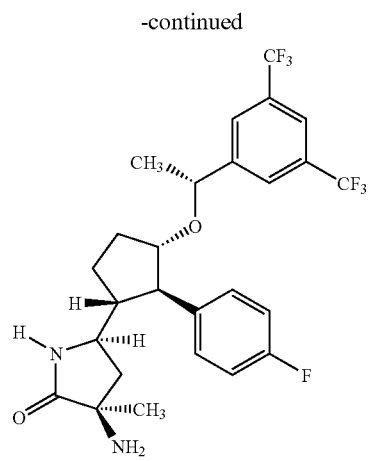
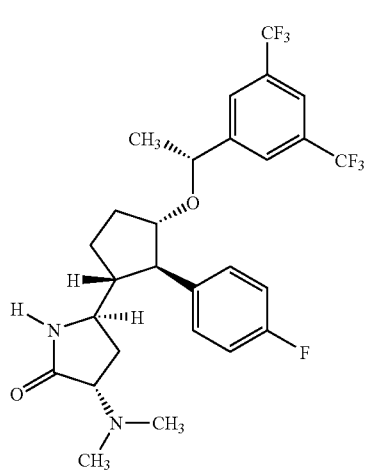
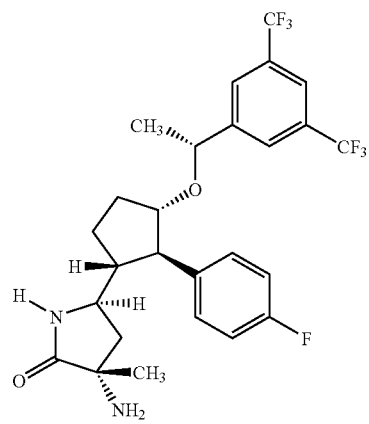
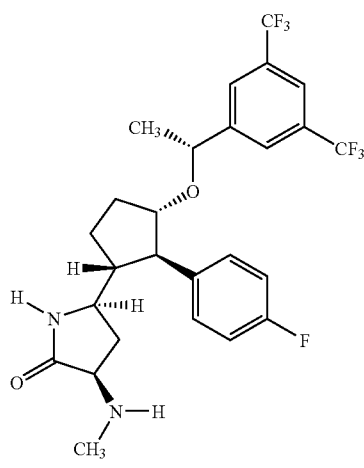
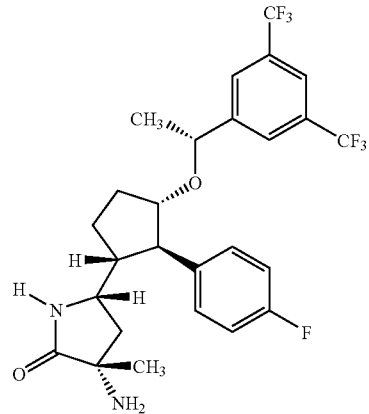

-continued

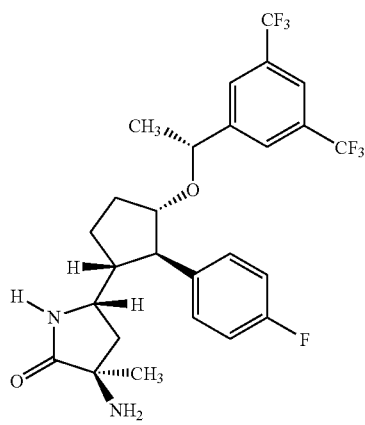

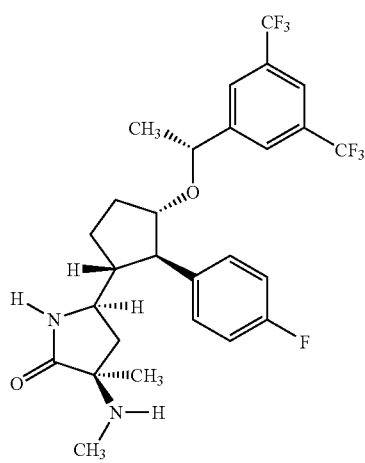

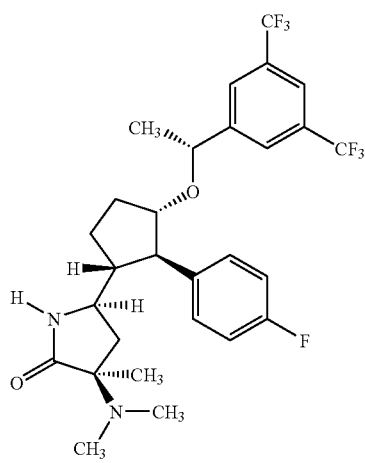

or a pharmaceutically acceptable salts thereof.

8. A pharmaceutical composition which comprises an inert carrier and a compound of claim 1 or a pharmaceutically acceptable salt thereof.

9. A compound which is

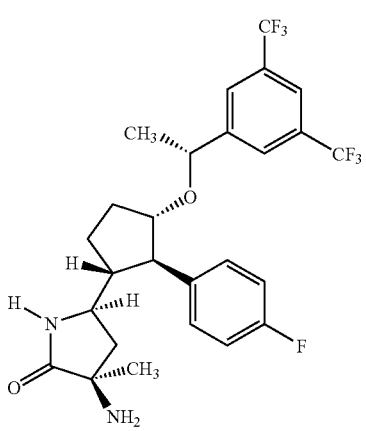

Ia

10. A method for the treatment of emesis in a mammal in need thereof which comprises the administration of a therapeutically effective amount of a compound according to claim 1.

11. A method for the treatment of urinary incontinence in a mammal in need thereof which comprises the administration of a therapeutically effective amount of a compound according to claim 1.

12. A method for the treatment of depression in a mammal in need thereof which comprises the administration of a therapeutically effective amount of a compound according to claim 1.

13. A method for the treatment of anxiety in a mammal in need thereof which comprises the administration of a therapeutically effective amount of a compound according to claim 1.

14. A method for the treatment of emesis in a mammal in need thereof which comprises the administration of a therapeutically effective amount of a compound according to claim 9.

15. A method for the treatment of urinary incontinence in a mammal in need thereof which comprises the administration of a therapeutically effective amount of a compound according to claim 9.

16. A method for the treatment of depression in a mammal in need thereof which comprises the administration of a therapeutically effective amount of a compound according to claim 9.

17. A method for the treatment of anxiety in a mammal in need thereof which comprises the administration of a therapeutically effective amount of a compound according to claim 9.

18. A pharmaceutical composition which comprises an inert carrier and a compound of claim 9 or a pharmaceutically acceptable salt thereof.

* * * * *